(12) United States Patent
Sanders

(10) Patent No.: US 8,925,551 B2
(45) Date of Patent: Jan. 6, 2015

(54) METHOD AND DEVICE FOR THE TREATMENT OF OBSTRUCTIVE SLEEP APNEA AND SNORING

(75) Inventor: Ira Sanders, North Bergen, NJ (US)

(73) Assignee: Linguaflex, Inc., Weston, FL (US)

( * ) Notice: Subject to any disclaimer, the term of this patent is extended or adjusted under 35 U.S.C. 154(b) by 569 days.

(21) Appl. No.: 10/597,590

(22) PCT Filed: Feb. 28, 2005

(86) PCT No.: PCT/US2005/006430
§ 371 (c)(1),
(2), (4) Date: Jul. 31, 2006

(87) PCT Pub. No.: WO2005/082452
PCT Pub. Date: Sep. 9, 2005

(65) Prior Publication Data
US 2009/0014012 A1    Jan. 15, 2009

Related U.S. Application Data

(60) Provisional application No. 60/547,897, filed on Feb. 26, 2004.

(51) Int. Cl.
*A61F 5/56* (2006.01)
*A61N 1/36* (2006.01)
*A61N 1/05* (2006.01)

(52) U.S. Cl.
CPC . *A61F 5/566* (2013.01); *A61N 1/36* (2013.01); *A61N 1/0548* (2013.01); *A61N 1/05* (2013.01); *A61N 1/3601* (2013.01)

USPC .................................................. 128/848

(58) Field of Classification Search
CPC ............................. A61F 5/56; A61F 5/566
USPC ............. 128/848, 887; 600/237, 32, 30, 201, 600/206, 208, 217, 242, 238, 239, 240
See application file for complete search history.

(56) References Cited

U.S. PATENT DOCUMENTS

| | | | |
|---|---|---|---|
| 3,517,669 A | 6/1970 | Buono et al. | |
| 3,659,612 A | 5/1972 | Shiley et al. | |
| 4,254,774 A * | 3/1981 | Boretos | 604/271 |
| 4,335,723 A | 6/1982 | Patel | |
| 4,387,879 A | 6/1983 | Tauschinski | |
| 4,704,111 A | 11/1987 | Moss | |

(Continued)

FOREIGN PATENT DOCUMENTS

| | | |
|---|---|---|
| DE | 197 56 956 | 7/1999 |
| JP | 2000-060862 | 2/2000 |

(Continued)

OTHER PUBLICATIONS

Doghramji, K., M.D. et al., *Predictors of Outcome for Uvulopalatopharnygoplasty*, Laryngoscope, vol. 105, pp. 311-314, 1995.

(Continued)

*Primary Examiner* — Victoria J Hicks
(74) *Attorney, Agent, or Firm* — Proskauer Rose LLP

(57) ABSTRACT

The device relates to methods and devices for the treatment of obstructive sleep apnea syndrome.

46 Claims, 16 Drawing Sheets

A

B

C

D

(56) References Cited

U.S. PATENT DOCUMENTS

| | | |
|---|---|---|
| 4,907,602 A | 3/1990 | Sanders |
| 4,981,477 A | 1/1991 | Schon et al. |
| 5,109,850 A | 5/1992 | Blanco et al. |
| 5,190,053 A | 3/1993 | Meer |
| 5,376,110 A | 12/1994 | Tu et al. |
| 5,464,395 A | 11/1995 | Faxon et al. |
| 5,480,420 A | 1/1996 | Hoegneld et al. |
| 5,498,247 A | 3/1996 | Brimhall |
| 5,591,216 A | 1/1997 | Testerman et al. |
| 5,694,922 A | 12/1997 | Palmer |
| 5,792,067 A | 8/1998 | Karell |
| 5,797,913 A | 8/1998 | Dambreville et al. |
| 5,843,021 A | 12/1998 | Edwards et al. |
| 5,954,050 A | 9/1999 | Christopher |
| 5,961,440 A * | 10/1999 | Schweich et al. ............... 600/16 |
| 5,976,109 A | 11/1999 | Heruth |
| 5,988,171 A | 11/1999 | Sohn et al. |
| 5,989,244 A | 11/1999 | Gregory et al. |
| 5,997,567 A | 12/1999 | Cangelosi |
| 6,013,728 A | 1/2000 | Chen et al. |
| 6,161,541 A | 12/2000 | Woodson |
| 6,251,059 B1 | 6/2001 | Apple et al. |
| 6,267,775 B1 | 7/2001 | Clerc et al. |
| 6,408,851 B1 | 6/2002 | Karell |
| 6,409,720 B1 | 6/2002 | Hissong et al. |
| 6,439,238 B1 | 8/2002 | Brenzel et al. |
| 6,546,936 B2 | 4/2003 | Knudson et al. |
| 6,547,787 B1 | 4/2003 | Altman et al. |
| 6,558,321 B1 | 5/2003 | Burd et al. |
| 6,601,584 B2 | 8/2003 | Knudson et al. |
| 6,610,065 B1 | 8/2003 | Branch et al. |
| 6,618,627 B2 | 9/2003 | Lattner et al. |
| 6,636,767 B1 | 10/2003 | Knudson et al. |
| 6,636,769 B2 | 10/2003 | Govari et al. |
| 6,742,524 B2 | 6/2004 | Knudson et al. |
| 6,764,446 B2 | 7/2004 | Wolinsky et al. |
| 7,237,554 B2 * | 7/2007 | Conrad et al. ............... 128/897 |
| 7,337,781 B2 | 3/2008 | Vassallo |
| 2001/0050084 A1 | 12/2001 | Knudson et al. |
| 2001/0054428 A1 | 12/2001 | Knudson et al. |
| 2003/0069626 A1 | 4/2003 | Lattner et al. |
| 2003/0091328 A1 | 5/2003 | Ishii et al. |
| 2003/0125743 A1 | 7/2003 | Roman et al. |
| 2005/0004417 A1 | 1/2005 | Nelson et al. |
| 2005/0092332 A1 | 5/2005 | Conrad et al. |
| 2006/0207606 A1 | 9/2006 | Roue et al. |
| 2007/0144534 A1 | 6/2007 | Mery et al. |
| 2008/0021485 A1 | 1/2008 | Catanese, III. et al. |
| 2008/0066766 A1 | 3/2008 | Paraschac et al. |
| 2008/0078412 A1 | 4/2008 | Buscemi et al. |

FOREIGN PATENT DOCUMENTS

| | | |
|---|---|---|
| JP | 2008-526286 | 7/2008 |
| WO | 92/21291 | 12/1992 |
| WO | 97/21385 | 6/1997 |
| WO | 99/00058 | 1/1999 |
| WO | 99/32057 | 7/1999 |
| WO | 00/29063 | 5/2000 |
| WO | 03/092765 | 11/2003 |
| WO | 2004/064729 A2 | 8/2004 |
| WO | 2005/044158 A1 | 5/2005 |
| WO | 2005/082452 | 9/2005 |
| WO | 2005/110280 | 11/2005 |
| WO | 2007/064908 A2 | 6/2007 |
| WO | 2007/092865 | 8/2007 |

OTHER PUBLICATIONS

Horner, R., *Motor control of the Pharyngeal Musculature and Implications for the Pathogenesis of Obstructive Sleep Apnea*, Sleep, vol. 19, pp. 827-853, 1996.

Loube, D., M.D., *Technologic Advances in the Treatment of Obstructive Sleep Apnea Syndrome*, Chest, vol. 116, pp. 1426-1433, 1999.

Mickelson, S., M.D. et al., *Midline Glossectomy and Epiglottidectomy for Obstructive Sleep Apnea Syndrome*, Laryngoscope, vol. 107, pp. 614-619, 1997.

Powell, N., M.D. et al, *Radiofrequency Volumetric Tissue Reduction of the Palate in Subjects with Sleep-Disordered Breathing*, Chest, vol. 113, pp. 1163-1174, 1998.

Proffit, W., D.D.S., Ph.D., Muscle Pressures and Tooth Position: A Review of Current Research, Australian Orthodontic Journal, pp. 104-108, 1973.

Rotunda, A., M.D. et al., *Detergent Effects of Sodium Deoxycholate Are a Major Feature of an Injectable Phosphatidylcholine Formulation Used for Localized Fat Dissolution*, Dermatologic Surgery, vol. 30(7), pp. 1001-1008, 2004.

Strollo, P. et al., *Medical Therapy for Obstructive Sleep Apnea-Hypopnea Syndrome, Principles and Practice of Sleep Medicine*, 4th ed. pp. 1053-1065, 2005.

Treiber, E., M.D. et al., *Breast Deformity Produced by Morphea in a Young Girl*, Cutis, vol. 54, pp. 267-268, 1994.

Michael Freidman et al., "Minimally Invasive Single-Stage Multilevel Treatment for Obstructive Sleep Apnea/Hypopnea Syndrome", The Laryngoscope (Oct. 2007)vol. 117, pp. 1859-1863.

Yosef P. Krespi et al., "Hyoid Suspension for Obstructive Sleep Apnea", Operative Techniques in Otolaryngology—Head and Neck Surgery (Jun. 2002), vol. 13, No. 2 , pp. 144-149.

Sheldon M. Mintz et al., "A Modified Geniotomy Technique for Obstructive Sleep Apnea Syndrome", J. Oral Maxillofac Surgery (1995), vol. 53, pp. 1226-1228.

Ståle Nordgård et al., "One-year Results: Palatal Implants for the Treatment of Obstructive Sleep Apnea", Otolaryngology—Head and Neck Surgery (2007), vol. 136, pp. 818-822.

Robert W. Riley et al., "Surgery and Obstructive Sleep Apnea:Long-Term Clinical Outcomes", Operative Techniques in Otolaryngology—Head and Neck Surgery (Mar. 2007), vol. 122, No. 3, pp. 415-421.

B. Tucker Woodson, "A Tongue Suspension Suture for Obstructive Sleep Apnea and Snorers", Operative Techniques in Otolaryngology—Head and Neck Surgery (Mar. 2001), vol. 124, No. 3, pp. 297-303.

B. Tucker Woodson, MD., et al., "A Randomized Trial of Temperature-Controlled Radiofrequency, continuous Positive Airway Pressure, and Placebo for Obstructive Sleep Apnea Syndrome", Otolaryngology-Head and Neck Surgery (Jun. 2003), vol. 128, No. 6, pp. 848-861.

B. Tucker Woodson, MD., et al., "Pharyngeal Suspension Suture with Repose bone Screw for Obstructive Sleep Apnea", Otolaryngology—Head and Neck Surgery (Mar. 2000), vol. 122, No. 3, pp. 395-401.

Eugenio Vicente, MD., et al., "Tongue-Base Suspension in Conjunction with Uvulopalatopharyngoplasty for Treatment of Severe Obstructive Sleep Apnea; Long-Term Follow-Up Results," Laryngoscope (vol. 116); Jul. 2006, pp. 1223-1227.

International Search Report from PCT/2005/06430 (1 pg.).

International Search Report to PCT/US2009/60991, Jan. 7, 2010, 3 pages.

* cited by examiner

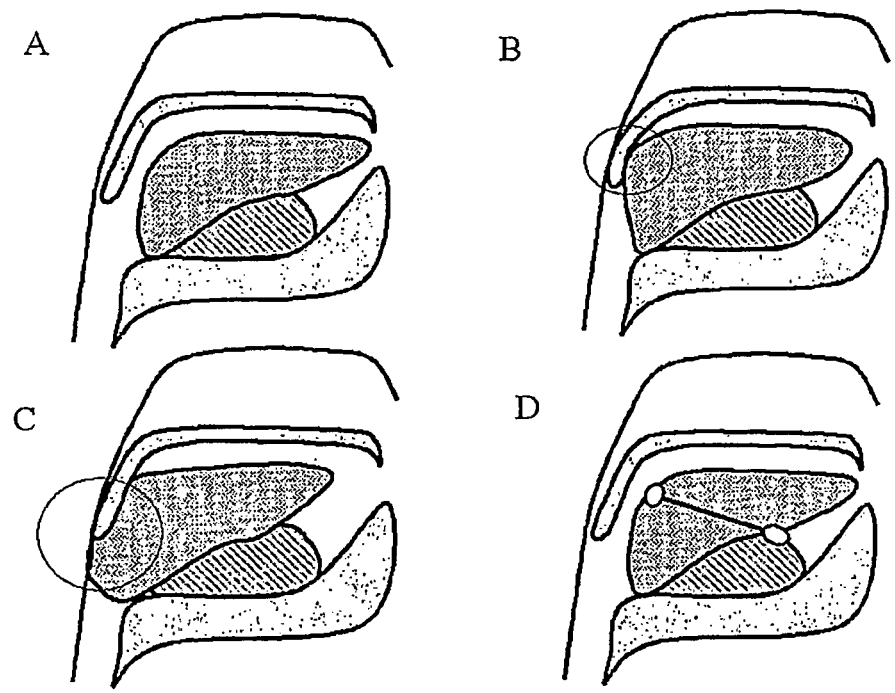
Figure 4. A,B,C,D

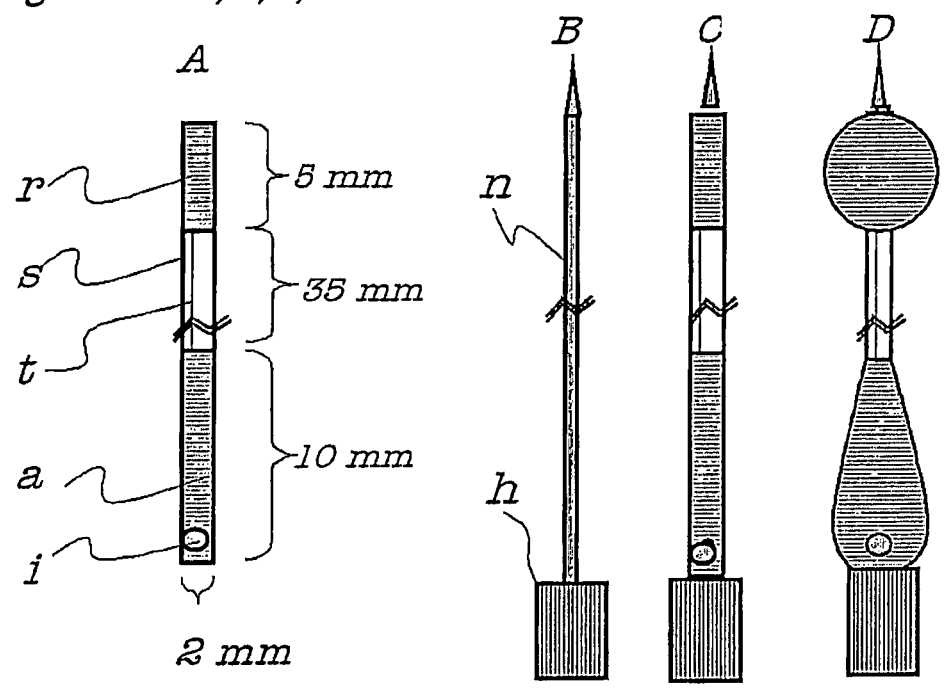

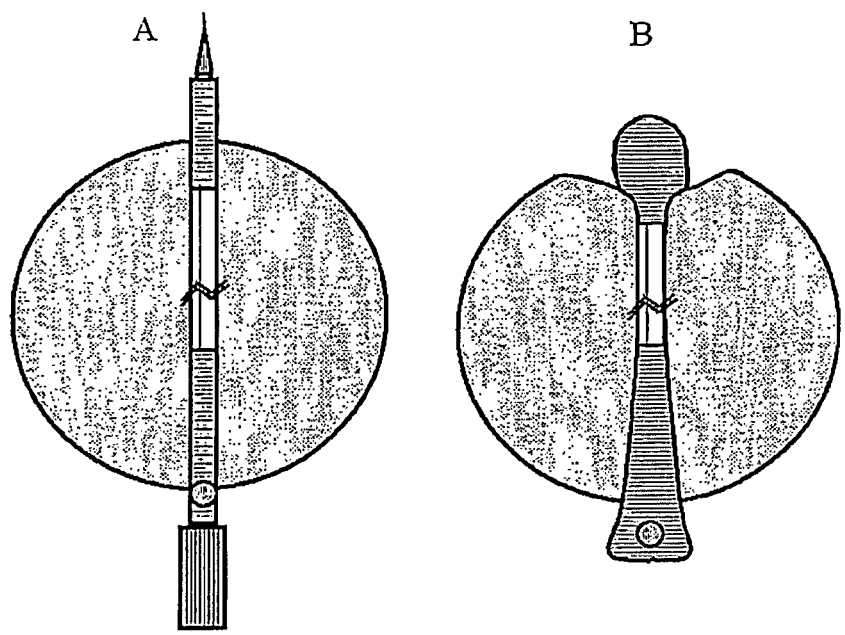
Figure 6 A,B

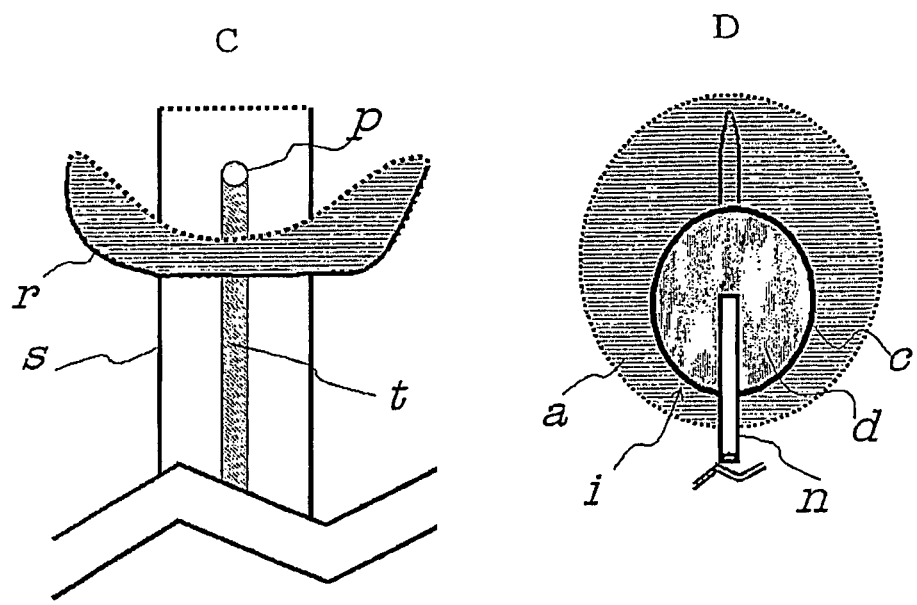

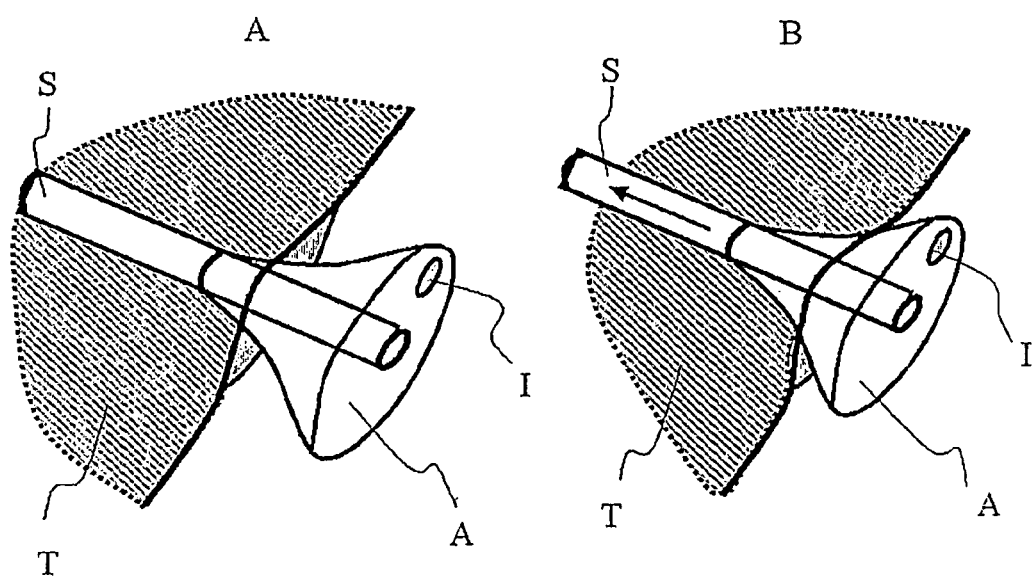
Figure 7 A,B

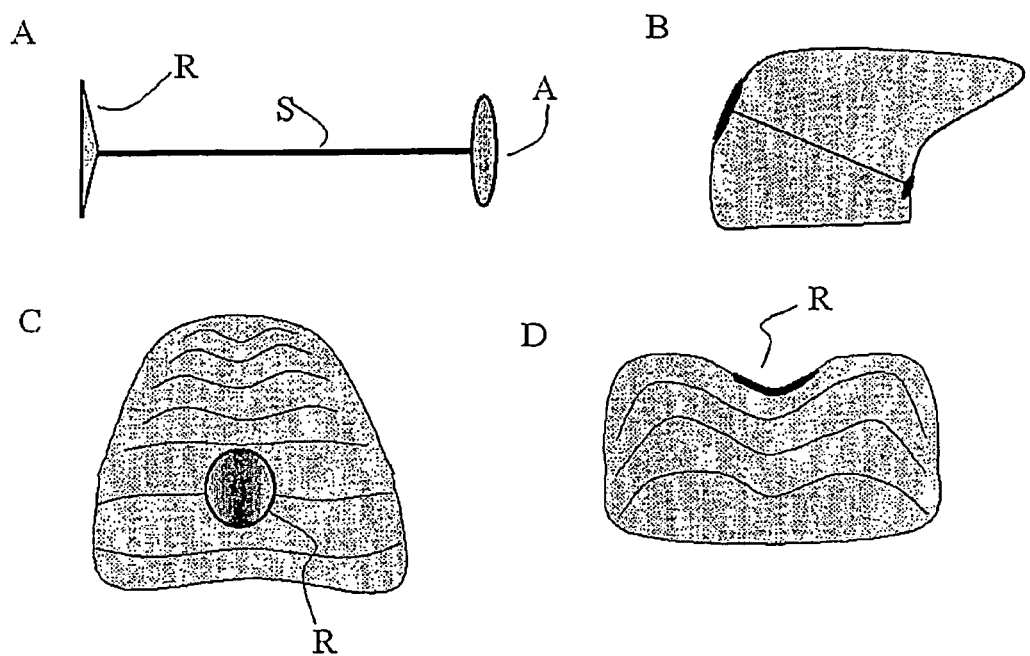
Figure 8. A,B,C,D

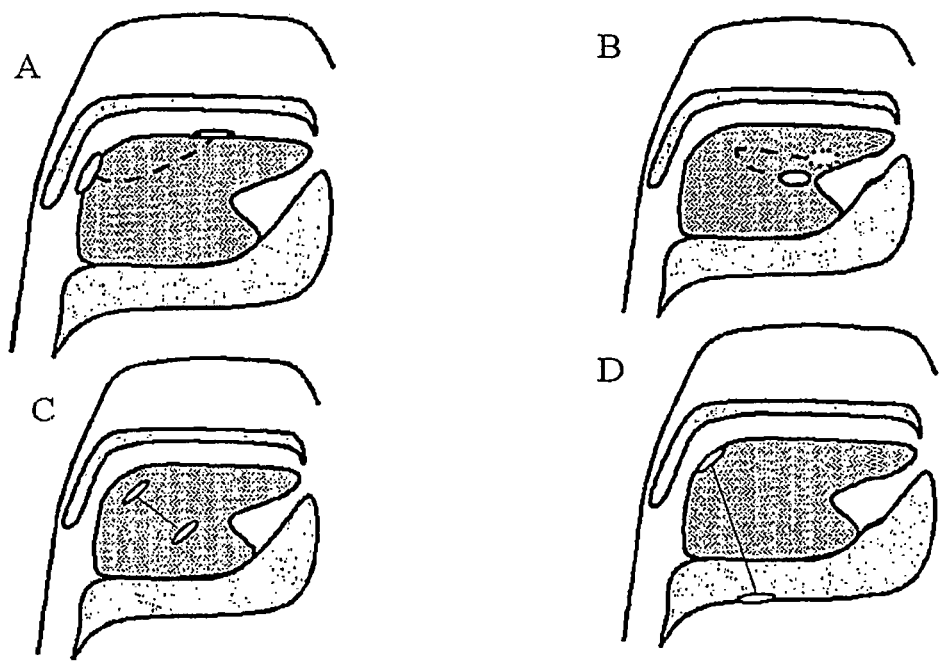
Figure 9. A,B,C,D

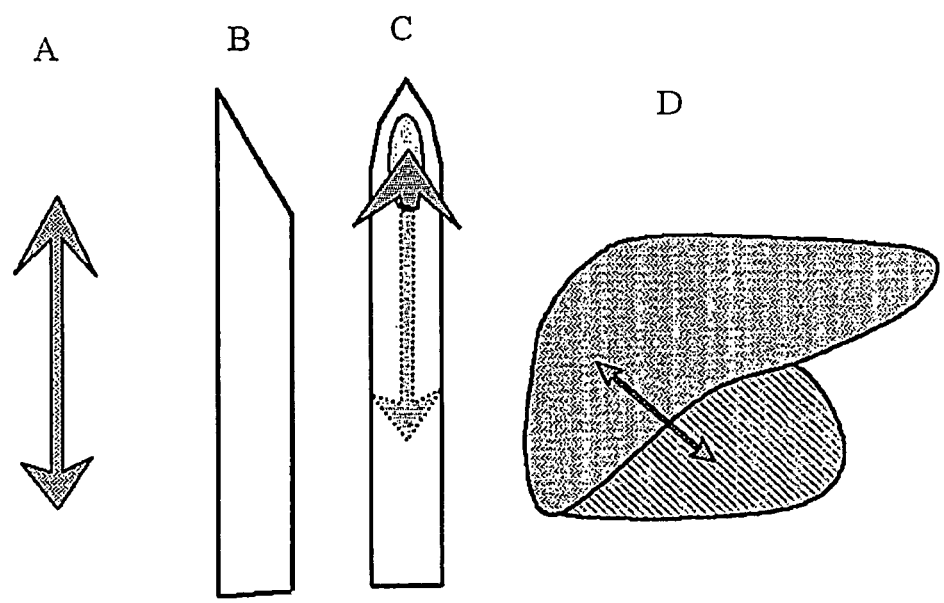
Figure 11. A, B, C, D

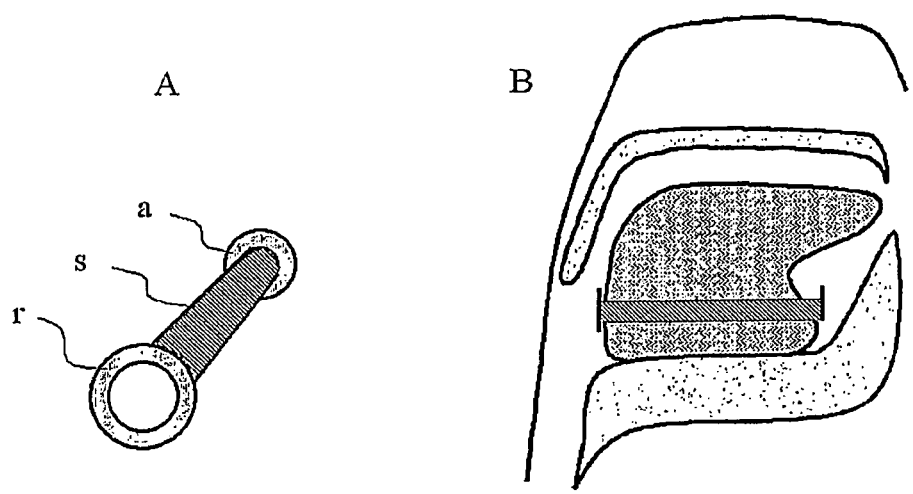
Figure 12. A,B

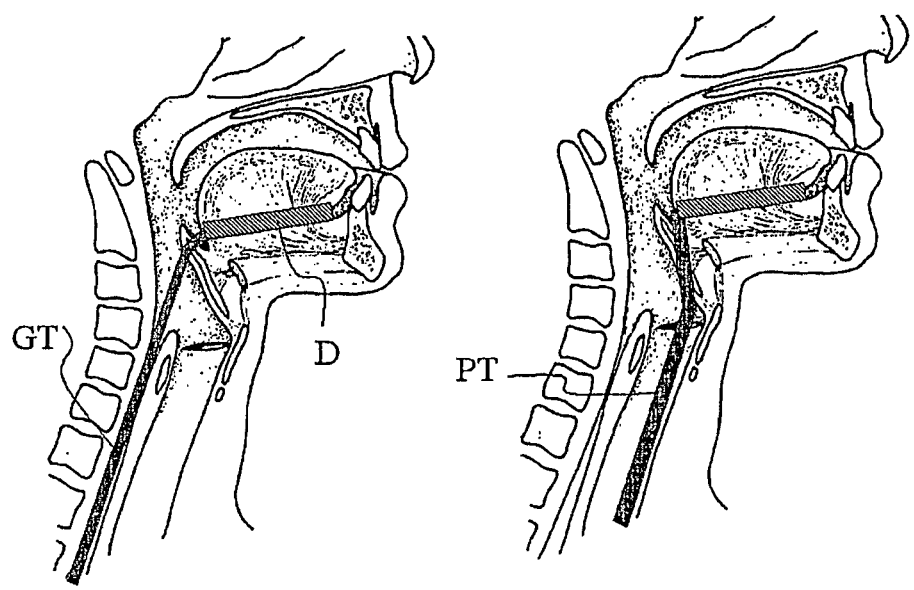
Figure 13. A, B

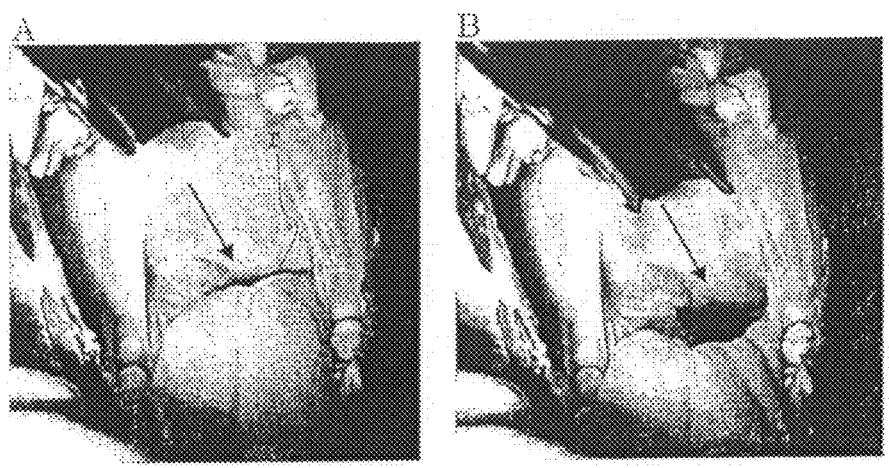
Figure 14. A,B

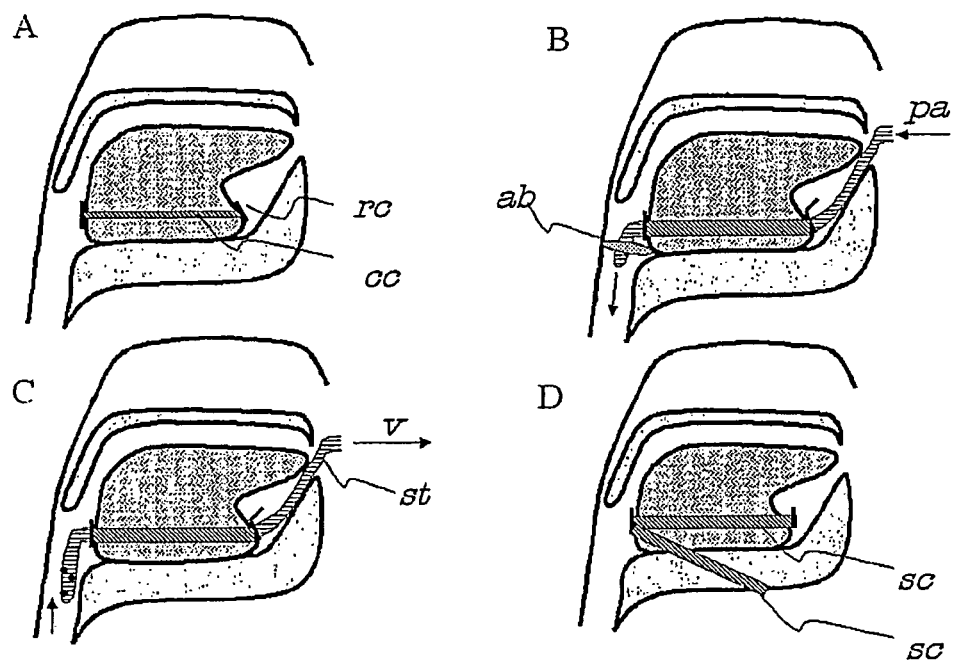
Figure 15 A,B,C,D

METHOD AND DEVICE FOR THE TREATMENT OF OBSTRUCTIVE SLEEP APNEA AND SNORING

CROSS REFERENCE RELATED APPLICATION

This patent claims priority to provisional patent No. 60/547,897 filed Feb. 26, 2004. All references are incorporated in entirety.

FIELD OF THE INVENTION

The invention relates to methods and devices for the treatment of obstructive sleep apnea syndrome by retraction of soft tissue in the oral cavity and pharynx. The invention also relates to devices implanted within the tongue that are used for diagnosis and treatment of medical disorders.

BACKGROUND

Snoring, upper airway resistance syndrome, and obstructive sleep apnea syndrome (OSAS) are all breathing disorders related to narrowing of the upper airway during sleep. Approximately 18 million Americans have sleep disordered breathing, but fewer than 50% are presently being diagnosed. More than 50% of Americans over age 65 have sleep difficulties, and prevalence of sleep problems will therefore increase as the over-65 population increases. Each year, sleep disorders, sleep deprivation, and excessive daytime sleepiness add approximately $16 billion annually to the cost of health care in the U.S., and result in $50 billion annually in lost productivity.

Pathophysiology of Sleep Disorders

Sleep disorders are largely caused by too much soft tissue in the throat. Humans are unique because their upper airway has a curved shape, an anatomical change that is related to the evolution of human speech. As a result the upper airway of humans is more flexible than other species and is more prone to collapse under negative pressure. In the awake state a certain amount of tone is present in upper airway muscles to prevent this collapse. However, during sleep muscle tone decreases in upper airway muscles and in certain susceptible individuals this relaxation allows the airway to collapse (Horner R L. Motor control of the pharyngeal musculature and implications for the pathogenesis of obstructive sleep apnea. *Sleep* 1996; 19: 827-853).

The upper airway refers to the air filled spaces between the nose and the larynx (FIG. 1). The most relevant part of the upper airway for sleep disorders is the air cavity called the pharynx. The pharynx can be divided into three anatomical levels (FIG. 2):
1) The nasopharynx is the part of the pharynx in the back of the nasal cavity.
2) The velopharynx corresponds to that part of the pharynx containing the velum (soft palate) and tongue curve.
3) The hypopharynyx is behind the tongue base.

The velopharynx is more susceptible to collapse because there are more soft tissue structures, leaving less room for airflow. The major structures of the velopharynx are the soft palate and the tongue, both of which are very flexible. The soft palate acts as a barrier between the mouth and the nose. In many people it is longer than necessary and extends down between the tongue and pharyngeal wall. The tongue is the largest muscular organ of the upper airway and is anatomically divided into a blade, body and base (FIG. 3). Most of the tongue's curve is at the junction of the tongue body and base.

In the awake condition the structures of the velopharynx maintain their shape because of continuous tone of their internal muscles. When this tone decreases, such as during sleep, these structures become quite flexible and distensible. Without the normal muscle tone that keeps them is place, they tend to collapse at relatively low negative pressures. Although muscles relax throughout the body during sleep many of the respiratory muscles remain active. Specifically, the major muscle that pulls the tongue forward, the genioglossus muscle, has been reported to show decreased activity during sleep, although it is active during obstructive apneas. Normally the genioglossus is capable of moving the tongue forward and even projecting it out of the mouth. Why the genioglossus muscle fails to prevent obstructions has not been explained.

During inspiration the chest wall expands and causes negative pressure to draw air into the nose and mouth and past the pharynx into the lungs. This negative pressure causes upper airway soft tissue to deform, further narrowing the airway. If the airway narrows enough the air flow becomes turbulent causing the soft palate to vibrate. The vibration of the soft palate produces the sound known as snoring. Snoring is extremely common effecting up to 50% of men and 25% of women. By itself snoring is not a medical problem although it can be a tremendous problem for the snorer's bed partner and a major cause of marital strain.

A small amount of decreased airflow or brief obstructions occurs in all humans during sleep. These episodes are counted as medically significant if airflow is decreased more than 50% of normal (hypopnea) or if airflow is obstructed for more then 10 seconds (apnea). The number of apneas and hypopneas that occur during each hour of sleep is measured to diagnose the severity of the sleep disorder. These episodes of hypopnea or apnea often cause some degree of arousal during sleep. Although the patient does not awaken to full consciousness, the sleep pattern is disturbed causing the patient to feel sleepy during the day. If the frequency of hypopnea or apnea is more than 5 episodes an hour it is called upper airway resistance syndrome. These patients often show symptoms related to the sleep disruption. Specifically, these patients are excessively sleepy during the day. In addition more subtle symptoms such as depression and difficulty concentrating are also common.

Technically the diagnosis of OSAS is defined as an average of more than 10 episodes of hypopnea or apnea during each hour of sleep. Although the airway is obstructed the patient makes repeated and progressively more forceful attempts at inspiration. These episodes are largely silent and characterized by movements of the abdomen and chest wall as the patient strains to bring air into the lungs. Episodes of apnea can last a minute or more, and during this time the oxygen levels in the blood decrease. Finally, either the obstruction is overcome, usually producing a loud snore, or the patient awakes with the feeling of choking.

Very common symptoms in OSAS patients are morning headaches and acid reflux. During airway obstructions the forceful attempts to inspire air can cause tremendous negative pressure in the chest. These high negative pressures can draw acid up the esophagus from the stomach. The acid can travel all the way into the mouth and cause inflammation of the vocal cords and nasal mucosa. The presence of the acid in the upper airway causes reflex bronchoconstriction in the lung that is similar to an asthma attack. If even a small amount of acid enters the lung it can cause the vocal folds to close tightly and itself cause a prolonged apnea called laryngospasm. In many patients the repeated stretching of the esophageal sphincter causes chronic changes and these patients can have acid reflux during the day.

Most importantly, sleep disorders can cause serious medical problems and death. Apneas cause a large strain on the heart and lungs. Over time repeated episodes of apnea cause chronic changes leading to hypertension. Long periods of apnea allow the oxygen levels in the blood to decrease. In turn the low oxygen can cause heart attacks or strokes.

Treatment of Sleep Disorders

Although OSAS occurs in both children and adults the cause and treatment are very different. OSAS in children almost always occurs when the child has large tonsils, and tonsillectomy cures the condition. Tonsils naturally decrease in size with age and are rarely a problem in adults. Instead susceptible adults usually have enlargement of their tongues, soft palate and/or pharyngeal walls. This enlargement is mostly due to fat deposits within these structures.

Adult sleep disorders are difficult to treat for a variety of reasons. The upper airway is a very mobile structure that performs the critical functions of swallowing and speech. These functions are easily compromised by surgical procedures or other interventions. In addition, the upper airway also has a large amount of sensory innervation that causes reflexes such as gagging and coughing. Theoretically a physical stent that is placed in the oral cavity and pharynx would be completely effective in relieving sleep apnea. When a patient is totally unconscious, such as when they are anesthetized for surgery, the airway can be stented open by placing a curved oral tube into the mouth and pharynx. In addition, endotracheal tubes establish a secure airway for artificial ventilation. However, after anesthesia wears off, patients immediately sense and react to the foreign objects in their throats and expel them. Therefore devices such as oral and endotracheal tubes, or anything similar, cannot be used for the treatment of OSAS.

Although physical stents cannot be used for OSAS an indirect way of stenting the upper airway with positive air pressure is the most commonly prescribed treatment for OSAS. This method is called continuous positive airway pressure (CPAP). CPAP requires the use of a mask tightly attached around the nose and connected to a respirator. The exact amount of positive pressure is different for each patient and must be set by overnight testing using multiple pressures. The positive pressure acts like a stent to keep the airway open. CPAP is not a cure but a therapy that must be used every night. Although many OSAS patients are helped by CPAP it is not comfortable for the patient or their bed partner. Patients often cannot tolerate the claustrophobic feeling of a mask tightly attached to their face. In addition there are often many technical problems with maintaining a proper seal of the mask to the face. For these reasons up to half of all patients who are prescribed CPAP stop using it within 6 months (Sanders, "Medical Therapy for Sleep Apnea," Principles and Practice of Sleep Medicine, 2nd Edition, pp. 678-684).

Tracheotomy

The only completely effective surgical therapy for OSAS is to bypass the entire upper airway by performing a permanent tracheotomy, a surgical procedure that forms a direct connection to the trachea through the neck. This is a dangerous procedure reserved for the worst cases when there is a high risk of serious medical complications from OSAS. Notably, temporary tracheotomies are often performed on patients with severe OSAS to control the airway before performing before any other procedure is performed on their upper airway. The reason is that these patients are at high risk of acute airway obstruction and death if there is any swelling in their airways. Due to the tremendous excess of swollen tissue in their upper airways OSAS patients are very difficult to intubate under emergency conditions. Similarly there is tremendous amount of fat in the neck that makes emergency tracheotomies extremely hazardous.

Prior to current conservative measures, postoperative deaths were not uncommon in severe OSAS patients. Moreover these patients often have acclimated to breathing against resistance, and when the resistance is suddenly removed their respiratory drive decreases. Even today the standard of care in treating most OSAS patients is to have them under close observation in an intensive care unit or recovery room after surgical procedures.

Soft Palate Procedures for Snoring

As the soft palate vibrates more than other tissues it plays a disproportional role in snoring. Various surgical therapies are available that shrink or stiffen the soft palate. The main procedure used is called uvulopalatopharyngoplasty [UPPP]. UPPP excises excess soft tissue of the pharyngeal walls and soft palate with a surgical scalpel. Because so much mucosa of the pharyngeal area is traumatized during a UPPP there is a large amount of post operative swelling and severe pain. In selected patients who snore but have no obstructions more limited versions of the UPPP can be done with lasers or electrical cautery.

Newer procedures minimize trauma to the mucosa and use needles to reach the underlying soft tissue to shrink its volume or stiffen it so that it resists vibration. Electrodes can be inserted into the soft palate to deliver radiofrequency energy that shrinks or stiffens the palate (Powell, N B, et al (1998) Radiofrequency volumetric tissue reduction of the palate in subjects with sleep-disordered breathing. Chest 113, 1163-1174.) (Somnoplasty; Somus; Mountainview, Calif.). Mild caustic agents can be injected that decrease the volume of the soft palate. U.S. Pat. No. 6,439,238 to Benzel teaches the application of a stiffening agent to the surface of the soft palate. Most recently, office based implantation of plastic inserts to stiffen the soft palate has been approved by the FDA (Pillar® Procedure, U.S. Pat. No. 6,546,936: Method and apparatus to treat conditions of the naso-pharyngeal area).

The fundamental shortcoming of all procedures that target the soft palate, including the newer techniques, is that they only partially improve OSAS (Loube DI (1999) Technologic Advances in the Treatment of Obstructive Sleep Apnea Syndrome. Chest. 1999; 116:1426-1433, Doghramji, K, et al (1995) Predictors of outcome for uvulopalatopharyngoplasty. Laryngoscope 105, 311-314). Although studies report a decrease in the number of apneas these patients are rarely cured. Evidently the critical structure causing OSAS is not the soft palate but the tongue.

Tongue Base Procedures for OSAS

The methods used to treat the tongue base in OSAS are either to permanently decrease its volume, to decrease its flexibility or to move the entire tongue forward.

Surgical excision of the tongue base has been poorly effective. The results for scalpel or laser resection of the tongue base in OSAS treatment have not been good enough to recommend continued application of these procedures (Mickelson, S A, Rosenthal, L (1997) Midline glossectomy and epiglottidectomy for obstructive sleep apnea syndrome. Laryngoscope 107, 614-619). More recently radiofrequency (U.S. Pat. No. 5,843,021 to Edwards) and ultrasonic (U.S. Pat. No. 6,409,720) energy have been proposed to shrink and stiffen the tongue base. The energy is delivered via needle electrodes that are inserted into the tongue base to cause a lesion that scars and shrinks over time. To avoid postoperative swelling and pain a limited amount of lesioning is done in a single session and patients require an average of 5 treatments. About a third of patients have greater than 50% improvement in their OSAS. However, approximately a fourth of patients have significant post operative complications, including tongue base ulcerations and abscesses, and temporary tracheotomy.

A recent introduced device for tongue base advancement is the Repose® system (Influent Corp; San Francisco, Calif.). The Repose® procedure is performed under general anesthesia, and a screw is inserted at the base of the mandible. The screw contains attachments for a permanent suture that is tunneled under the mucosa of the floor of the mouth to the back of the tongue, then passed across the width of the tongue base, and brought back to attach to a metal hook screwed into the bone of the mandible. The suture is tightened to displace the tongue base forward, and caution must be observed to prevent excess tension leading to necrosis of tissue. Unfortunately studies of the Repose® procedure show that it is ineffective at eliminating OSAS. Only 1 of 15 patients was cured of OSAS while 2 patients had to have the suture removed due to pain and swelling.

More aggressive surgical procedures require reconstruction of the mandible, facial, skeleton or the hyoid bone. An example of the art is U.S. Pat. No. 6,161,541 to Woodson that teaches a method of surgically expanding the pharyngeal airway. These procedures require extensive surgery with higher risks and much longer recovery periods.

Other proposed methods for treating the tongue base include stiffening the soft tissue by injection of sclerosing particles U.S. Pat. No. 6,742,524 (Method and apparatus to treat conditions of the naso-pharyngeal area) or other implanted material US patent application No. 20050004417A1 (Devices, systems, and methods to fixate tissue within the regions of body, such as the pharyngeal conduit).

Neuroprosthetic Devices

Various neuroprosthetic devices have been invented that stimulate upper airway muscles. U.S. Pat. No. 4,907,602 to Sanders describes transmucosal stimulation to dilate the airway; U.S. Pat. No. 5,792,067 to Karell teaches an intraoral device that applies electrical stimulation to the hard palate, soft palate or pharyngeal area to induce contraction of the upper airway muscles; U.S. Pat. No. 5,190,053 to Meer teaches an intraoral device that applies electrical stimulation to the genioglossus muscle via electrodes located on the mucosa on the floor of the mouth on either side of the frenulum. In addition U.S. Pat. No. 5,591,216 to Testerman describes a totally implantable device to stimulate the nerves to the genioglossus muscles. In addition, WIPO application No 04064729 to Gordon describes a neuroprosthetic device that can be injected into the soft palate to treat snoring. At present these devices have not been clinically proven.

In summary, sleep disorders are a significant health problem without an acceptable solution and there is a need in the art for new and more effective therapies.

While not wishing to be bound by theory my studies of human tongue anatomy suggest that episodes of obstruction evolve by a sequence of events (FIG. 4). The initial inciting event is the deformation of a relatively small part of the tongue. Under certain conditions deformation begins in soft tissue on the top of the tongue, particularly in the area of the tongue curve, and specifically near the center line of the tongue curve. As this tissue deforms it narrows the airway and causes more negative pressure thereby causing greater deformation. This feedback cycle in turn deforms enough tissue in the area to cause a complete obstruction in the velopharyngeal area.

If an initial obstruction occurs near the end of inspiration, the obstruction is relieved by an expiration, or by action of the genioglossus muscle. However, if the obstruction occurs at the beginning of inspiration reflexes trigger stronger inspiratory effort that further lowers airway pressure. This increased negative pressure causes deformation and collapse of most of the tongue base. At this point the airway is firmly plugged by soft issue and activity of the genioglossus only stretches the tongue tissue that is plugged and cannot dislodge it.

Therefore the tongue curve is the critical area that initiates the cascade leading to obstruction. This relaxed muscle is very flexible and easy to deform, however, the converse is also true, and very little force is needed to prevent this deformation. Therefore if sufficient counterforce is exerted at the proper localized area of the tongue it can prevent obstruction without noticeable effects on speech and swallowing movements.

How a device could prevent the deformation and collapse of the tongue curve is not a trivial problem:
  This area of the tongue is very mobile during speech and
    swallowing, therefore the amount of force exerted must
    be low and highly localized. It is unacceptable to render
    the area immobile, as would be done if were stiffened by
    a large implant or scar tissue.
  Moreover the whole area of the velopharynx has extensive
    sensory innervation, and relatively minor stimulation
    there causes either a gag or a swallow.
  In addition the tongue base and body have a larger blood
    supply than comparable muscles elsewhere in the body.
    Any implant placed in the area has a high probability of
    causing internal bleeding with potentially catastrophic
    tongue swelling.
  Finally, OSAS patients have borderline airways that can
    obstruct after even minor amounts of swelling such as
    that following surgical manipulation. Therefore it not
    obvious how a device could both exert force in the area
    yet avoid swelling.
Moreover to be maximally effective and get patient and physician acceptance the device would ideally have additional qualities:
  It should be capable of being inserted as an outpatient
    procedure.
  Preferably the device could be removed during the day and
    reinserted by the patient at night.
  It would be adjustable to conform to the specific needs of
    the patient.
  It would be comfortable for the patient.
  When the device was in place it would not be noticeable to
    anyone else.

SUMMARY OF THE INVENTION

The invention comprises a method and device for the treatment of OSAS and its symptoms such as snoring. In the preferred embodiment the device is inserted into the tongue to treat patients with OSAS. This patient population has serious medical problems and few treatment options.

The method counteracts the deforming influence of negative airway pressure on the relaxed soft tissue of upper airway structures. These structures include, without limitation, the tongue, soft palate, pharyngeal walls and supraglottic larynx. The soft tissue is retracted by a device implanted in tissue (FIG. 14). In turn the retractor is mechanically connected to another soft tissue site, preferably a muscle that continues to contract during inspiration. By this method the device effectively prevents airway obstruction during sleep. The device is composed of three distinct parts. A retractor is physically coupled to the relaxed soft tissue area. A shaft connects the retractor to an anchor. The anchor imparts counterforce through the shaft to the retractor, thereby preventing deformation of the soft tissue.

By extensive study of the internal anatomy of the tongue I have discovered that certain areas of the tongue have little or no vasculature or nerve structures. Most importantly the entire midline in the tongue body has few vital structures. In the preferred embodiment a device could be placed through the centerline of the tongue without risk of causing damage to blood vessels or nerves. Although there are other routes through the tongue that avoid vital structures the centerline is most preferred because the most deformable part of the tongue curve is along the centerline. Surprisingly then, a device can be placed directly through the tongue to the area most vulnerable to OSAS with minimal risk.

In the preferred embodiment the device comprises a hollow flexible shaft with an inflatable balloon at each end. To insert the device it is slipped over a needle and the balloons are deflated. The combined device and needle then is passed directly through tongue tissue such that the retractor balloon presses on the base of the tongue while the anchor balloon provides counterforce by its design as well as its position in the genioglossus muscle. The mechanical counterforce prevents deformation of the relaxed tongue during sleep.

The device conveys enough force to maintain the tongue curve in its neutral position during sleep. However, during speech and swallowing the tongue base moves both forward and backward from the neutral position. These movements are quite strong, for example the movement of the tongue base during swallowing exerts about ten times more force than that needed to keep the relaxed tongue in the neutral position. Therefore the device is designed to limit its force and allow free movement of the tongue base during speech and swallowing.

An advantage of the invention over the prior art is that, unlike current surgical procedures and devices for OSAS, the invention acts on a small and localized area, rather than on the entire upper airway structure. Therefore the invention is effective without significantly impairing normal function. As the device is inserted by a needle there is minimal post procedure pain or swelling, therefore the procedure can be performed in an outpatient environment.

A further advantage over prior art is that as soon as the device is inserted it allows the physician to control the airway, imparting a level of security against serious complications. In an emergency it can be grasped at its anchor end under the tongue and manually retracted to enlarge the airway. This will help prevent the potentially lethal airway obstructions to which severe OSAS patients are susceptible.

Further advantages over prior art is that the device is adjustable and completely removable. Once the physician has made the initial insertion, and the tract matures, the device can be removed by the patient in the morning and reinserted at night. After insertion the patient can adjust the tension of the device for maximum effectiveness and comfort. As the device is inserted from beneath the tongue and exits near the tongue base it is not easily seen by other people. Finally, an advantage of the invention is that it is inexpensive relative to current treatments for OSAS.

Although the preferred embodiment of the invention is implanted in tongue, alternative embodiments can also be used to treat lax soft tissue of the soft palate, pharngeal walls and larynx that impinge on the airway.

Further alternative embodiments of the device have beneficial uses. If its shaft is hollow it serves as a conduit through the tongue. In this way a connection is made between the oral and pharyngeal cavities through which air pressure is equalized, thereby helping to prevent OSAS. Still further embodiments utilize the conduit to supply air at positive pressure to the pharynx.

In further alternative embodiments the open conduit can serve as an easy pathway for accessing the pharyngeal cavity and neighboring structures. Catheters can be passed to suction secretions from the pharynx and lungs, or pass feeding tubes into the stomach. Endoscopic surgical instruments can be passed into the pharynx and neighboring structures to perform surgical procedures.

In further alternative embodiments the conduit can serve to store medical sensing or diagnostic instruments or pass them into the pharynx. Examples include sensing oxygen or carbon dioxide levels of arterial or venous blood, airflow or vibration. These sensors can transmit physiological data to a receiver outside the body or used to control other implanted medical devices.

It is an object of the invention to provide a conduit to house therapeutic equipment such as neuroprosthetic sensors and/or stimulators. These could be used to stimulate the tongue nerves or muscles to improve swallowing or speech function of the tongue.

Finally, drugs can be stored in the conduit and to be delivered locally to the mouth or pharynx; non-limiting examples are antibiotics for periodontal disease and antifungal medication for oral candidiasis. Alternatively the drugs could be released across the walls of the device into surrounding tissue. As there is tremendous blood supply to the tongue the medication could enter the systemic circulation rapidly. Non limiting examples include insulin to treat diabetes and radioactive material or chemotherapeutic agents for therapy of cancer.

OBJECTS AND ADVANTAGES OF THE INVENTION

It is an object of the invention to provide a method and device for the treatment of OSAS.

A further object of the invention is to retract or prevent the deformation of tongue, soft palate, pharyngeal wall and/or laryngeal soft tissue, thereby treating OSAS.

It is an object of an alternative embodiment of the invention to provide a conduit through the tongue for therapeutic or diagnostic purposes.

BRIEF SUMMARY OF THE DRAWINGS

FIG. 4 is a mechanism of airway obstruction.

FIG. 5 is a tongue retractor.

FIG. 6. A, B is an insertion of device.

FIG. 6. C, D is an inflation mechanism for device balloons.

FIG. 7. A, B is an anchor balloon mechanism of action.

FIG. 8. A, B, C, D is an alternative embodiment of device.

FIG. 9. A, B, C, D is an alternative locations of the device in the tongue.

FIG. 11. A, B, C, D is a totally implanted embodiment of the device.

FIG. 12 is an Alternative embodiment of the device as a conduit.

FIG. 13. A, B is an Embodiment as a conduit for gastric and pulmonary tubes.

FIG. 14 is a retraction of tongue curve.

FIG. 15 A, B, C, D is the alternative embodiments as a collapsable conduit.

DETAILED DESCRIPTION OF THE DRAWINGS

Figure 1:
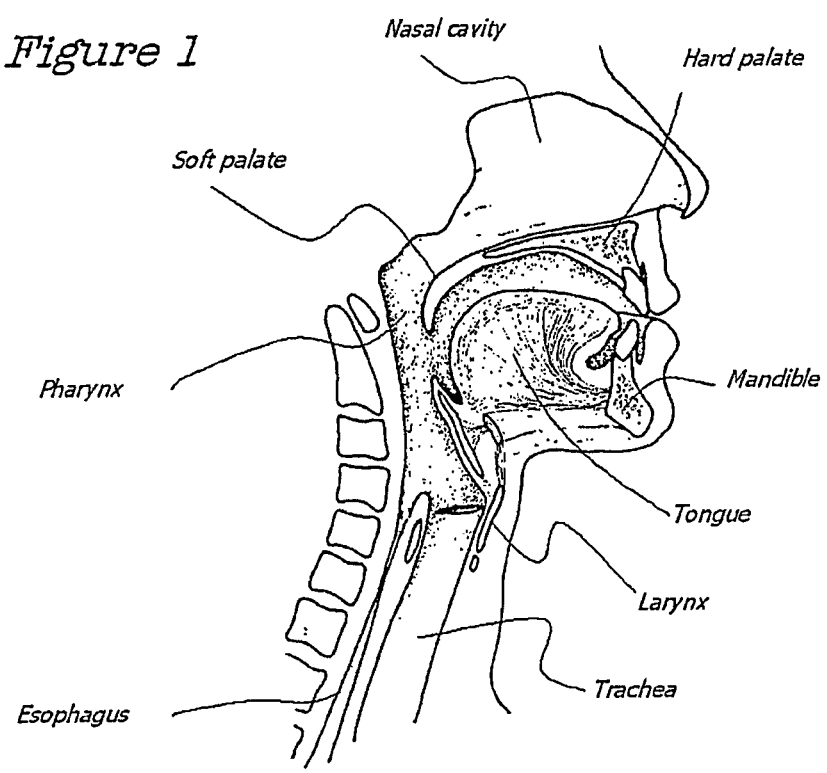
FIG. 1 is a drawing of the human upper airway in the mid saggital plane.
Figure 2:
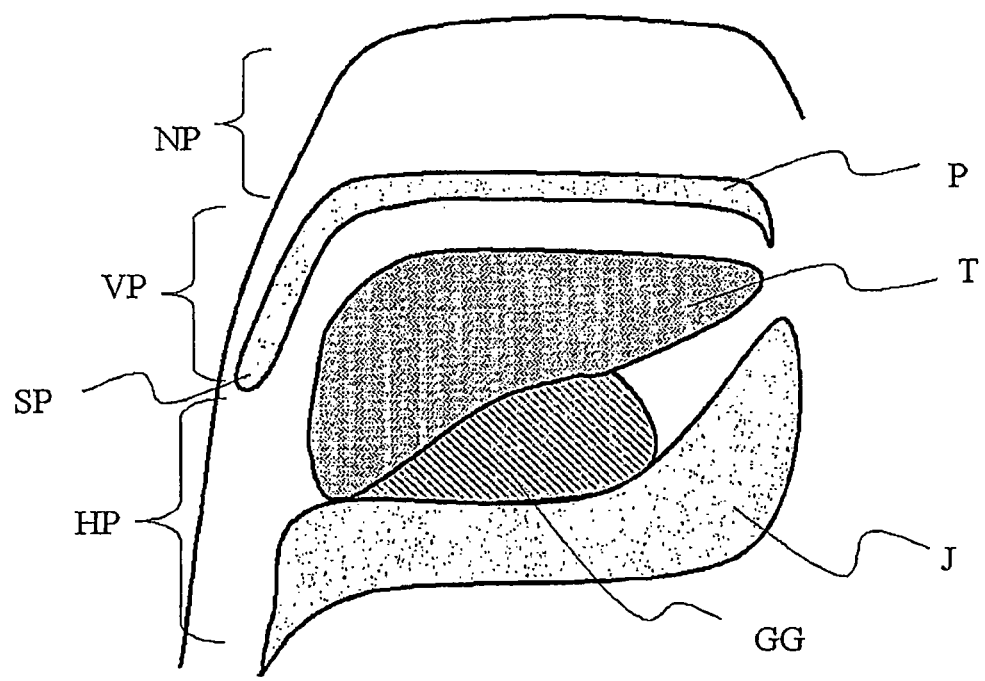
FIG. 2 is a simplified schematic drawing of the tongue and surrounding structures.
Figure 3:
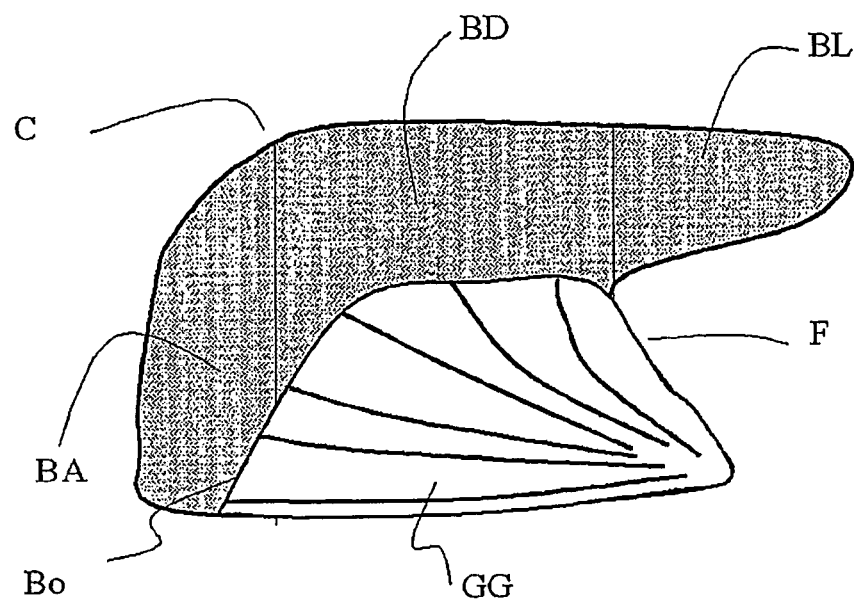
FIG. 3 is anatomical landmarks of the tongue.

FIG. 2. Simplified schematic drawing of the tongue and surrounding structures
NP, Nasopharynx
VP, Velopharyrnx
HP, Hypopharynx
SP, Soft palate
P, Hard palate
T, Tongue
GG, Genioglossus muscle FIG. 3. Anatomical landmarks of the tongue.

The part of the tongue that relaxes during sleep is shaded in this schematic drawing. The genioglossus muscle (GG), that does remain active during sleep, inserts into a connective tissue boundary on the undersurface of the tongue (Bo).
BA) Tongue base
BD) Tongue body
BL) Tongue blade
Bo) Boundary between tongue and genioglossus
C) Tongue curve
F) Frenulum
GG) Genioglossus muscle FIG. 4. Mechanism of airway obstruction.

A) Normal tone in tongue while awake. Tongue remains in position allowing airway to remain open.

B) During sleep muscle tone is lost and the soft tissue of the tongue becomes flaccid. Negative pressure in the pharynx during inspiration causes collapse of the tongue in the velopharyngeal area because the airway is narrowest at that point and the tongue curve (circle) is most deformable.

C) Once obstruction occurs at any point along the upper airway inspiration lowers the pharyngeal pressure causing collapse of other soft tissue structures, particularly the tongue base (circle).

D) Tongue retractor in place preventing posterior deformation of tongue curve.

FIG. 5. Tongue retractor.
r, retractor balloon,
s, shaft,
t, tube,
a, anchor,
i, injection port,
n, needle,
h, handle FIG. 6. A, B. Insertion of device.

The combined device and trocar is passed through the tongue (A). The balloons are then inflated to secure the device in place (B).

FIG. 6. C,D. Inflation mechanism for device balloons.

C) The balloons can be separately inflated but preferably they are connected by a small tube (t) that passes between them on the side of the shaft (s). The tube has an open port at its terminal end within each balloon thereby allowing free passage of fluid or air.

D) The anchor balloon is inflated or deflated by an injection needle that passes through a resealable diaphragm (d) and this diaphragm is held in place by a collar (c) that in turn connects to the balloon membrane. p, open end of tube d, diaphragm, c, collar.

FIG. 7. A,B. Anchor balloon mechanism of action.

Counterforce is adjustable by inflating or deflating the anchor balloon. Tongue tissue has some resistance to being separated. The anchor balloon has a wedge shape (A) that widens as pressure within the balloon increases. By this method the angle of the wedge can be increased, thereby causing a proportional increase in the tissue force against the anchor balloon, which is the counterforce conveyed to the retracting balloon via the shaft. The amount of counterforce needed to keep the relaxed tongue base in position is low. While tongue movements such as swallowing exert very large forces as the tongue moves backward. At maximum inflation the anchor balloon still exerts much less counterforce than the tongue during swallowing. Therefore the anchor balloon can slide into the tongue tissue (7 B, arrow) to allow backward movement of the tongue base without impairing the normal tongue movements.

FIG. 8. A,B,C,D. Alternative embodiment of device.

There are multiple alternative embodiments of the device that do not use balloons or any hydraulic mechanism. Shown is an example of one embodiment.

FIG. 9. A,B,C,D. Alternative locations of the device in the tongue.

The device can be oriented in alternative locations within the tongue and yet achieve the goals of preventing tissue deformation. A) The retractor is placed at the tongue curve and the anchor is placed on the same side in tongue blade.

B) Two "anchor" ends on either side of frenulum. The shaft is flexible and loops beneath the tongue curve. In this embodiment the shaft functions like an implanted retractor.

C.) Entire device implanted within the tongue.

D) Device anchor outside of neck

Figure 10:
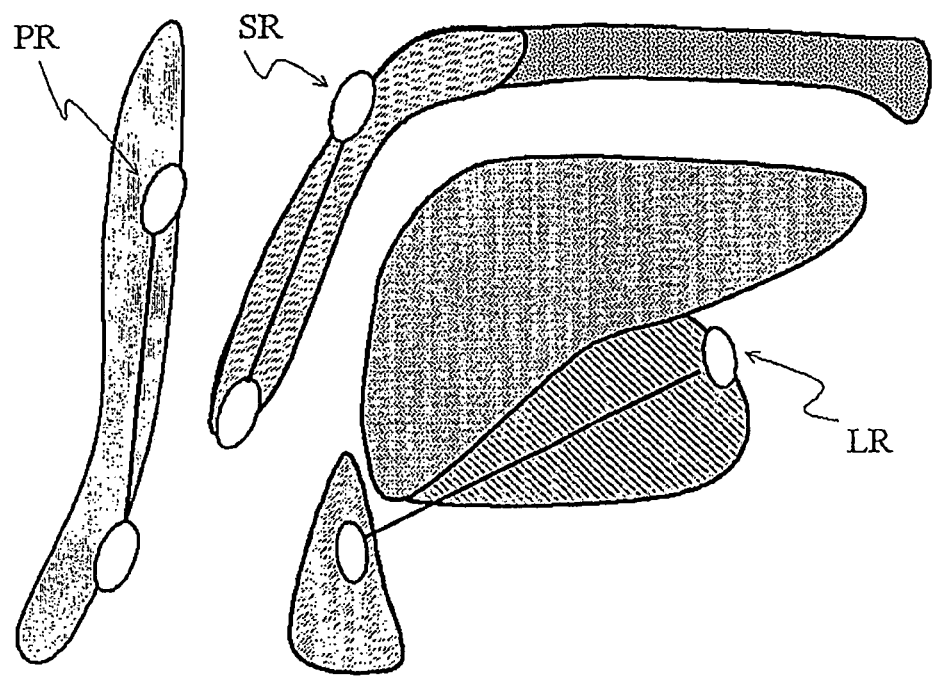
FIG. 10 is an alternative embodiments in other soft tissue organs.

FIG. 10. Alternative embodiments in other soft tissue organs.
PR, pharyngeal wall retractor;
SR, soft palate retractor;
LR, laryngeal soft tissue retractor FIG. 11. Alternative embodiment as a conduit FIG. 11. A,B,C,D. Totally implanted embodiment of the device.

In one alternative embodiment the entire device is implanted. Implanted devices can have anchor or retractor members that interact with tissue differently then those used on the mucosal surface. In this example the device both the retractor and anchor have an arrow shape, with the arrows acting as hooks. The shaft is 2 cm in length and is stretches easily. The entire device is preferably made a single continuous flexible structure. The device is inserted into the bore of needle (B side view of needle, C device inserted in needle). The needle is then inserted to the proper depth within tissue and withdrawn.

FIG. 12. Alternative embodiment of the device as a conduit.

FIG. 13. A,B. Embodiment as a conduit for gastric and pulmonary tubes.
GT, Gastric Tube
PT, Pulmonary tube FIG. 14. Retraction of tongue curve.

Shown is the oral cavity of a dog, the tongue is at the bottom of the photos and the palate is at the top. The arrow points to the airway. A) The flaccid tongue obstructs the airway. A prototype of the retactor has been inserted in the dog's equivalent of the tongue curve and only it's edge is visible {r}. With minimal counterforce on the retractor head the airway lumen is restored.

FIG. 15. Alternative embodiments as a collapsable conduit.

A) A device with flexible walls collapses after insertion (cc). The device maintains the conduit through the tongue. A resealable cap can be opened to pass medical devices through the conduit (rc).

B) Example of a ventilation tube passed through the conduit. An airway balloon (ab) can be inflated to form a seal so that the patient can be ventilated with pressurized air (pa).

C) Example of a suction tube (St) passed through the conduit. A vacuum source (v) suctions secretions from the pharynx.

D) Example of surgical conduits (sc) placed to allow passage of endoscopic surgical instruments into the pharynx and neighboring structures.

cc, collapsible conduit (cc)
rc, resealable cap
ab, airway ballon
pa, pressurized air
v, vacuum source
st, suction tube
sc, surgical conduit

DETAILED DESCRIPTION OF THE INVENTION

Definitions

"Tongue curve" refers to the area of the tongue where it's superior surface curves from a horizontal orientation (tongue body and blade) to a vertical orientation (tongue base). Preferably tongue curve refers to the soft tissue in this area between the mucosal covering of the tongue and the connective tissue boundary where the genioglossus muscle attaches.

"Tongue blade" refers to the part of the tongue anterior to the frenulum. It is covered by mucosa on its top, sides and undersurface.

"Tongue body" is the mid part of the tongue located between the tongue blade and tongue base.

"Tongue base" refers to the part of the tongue posterior to the tongue curve. In anatomical terms the line of demarcation of the tongue base is the circumvalatte papillae, a grossly visible line of raised taste organs on the superior surface of the tongue.

"Conduit" refers to one embodiment of the invention wherein the shaft is hollow and once implanted there is continuity between the air spaces on both ends of the device. Preferably these air spaces are the pharynx at the retractor end and the oral cavity at the anchor end.

"Collapsable conduit" refers to one embodiment of the invention where most components of the device, most preferably the shaft collapse after insertion due to surrounding tissue pressure. Preferable these conduits serve as guides for other devices to be passed through, preferably suction and feeding tubes, ventilation tubes, and endoscopic surgical devices.

"Frenulum" refers to the vertical anterior edge of the genioglossus muscle. The frenulum passes from the floor of the mouth up to the centerline of the underside of the tongue. The frenulum marks the boundary between the tongue blade and tongue body.

"Tongue boundary" or "boundary" is the inferior surface of the tongue bady and base. The genioglossus muscle inserts onto a large part of the boundary.

"Deformation" refers to an abnormal change in the shape of upper airway soft tissue structures. This deformation is preferably due to negative pressure acting on relaxed upper airway structures during sleep causing them to narrow the upper airway. Most preferably this soft tissue is the tongue curve.

"Reverse deformation" refers to a change in soft tissue shape caused by the tissue retractor. In some embodiments reverse deformation refers to restoring a deformed structure to its normal shape. In other embodiments reverse deformation refers to an indentation of soft tissue in a given area due to the action of a tissue retractor.

"Tissue retractor" refers to the complete device of the invention for the prevention of soft tissue deformation. The device may be used without limitation in the tongue, soft palate, or pharyngeal walls.

"Tongue retractor" refers to a complete device used for the prevention of tongue deformation. Preferentially it comprises a retractor connected to a shaft which in turn is connected to an anchor.

"Palate retractor" refers to a complete device used for the prevention soft palate deformation.

"Pharyngeal wall retractor" refers to a complete device for the prevention of pharyngeal wall deformation.

"Laryngeal retractor" refers to a complete device for the prevention of laryngeal soft tissue deformation.

"Retractor" or "retractor head" or "retractor member" refers to a part of the overall tissue retractor. The retractor physically interacts with soft tissue, either directly or indirectly, to prevent it from deforming. In certain embodiments the retractor head is a disc located on the external surface of the tongue, in other embodiments the refractor head is an inflatable balloon, in other embodiments the retractor head may have curved parts that act like hooks, in other embodiments the retractor head may be a flexible wire passing through the tissue. In some embodiments it may be totally implanted within tissue.

"Retractor shaft", "shaft" or "retractor member" refers to that part of the tongue retractor that attaches to the retractor head and serves to connect it to the retractor anchor. In some embodiments the retractor In different embodiments the shaft may be rigid or flexible, solid or hollow, one piece or multiple linked pieces.

"Retractor anchor", "anchor" or "anchor member" refers to a component of the device that physically interacts with tissue to provide counterforce to the retractor.

Example 1

Preferred Embodiment of the Invention

In its preferred embodiment the device is composed by a thin flexible hollow shaft with inflatable balloons as retractor and anchor members (FIG. 5 A). The materials and manufacture of such a device is well known in the art as exemplified by angioplasty catheters, tracheotomy tubes, jejunostomy tubes and other biocompatible medical devices that are temporarily or permanently implanted within body tissue. As representative examples of the art, U.S. Pat. No. 3,659,612 to Shiley describes a cannula that is placed in the trachea with a refillable balloon at its internal end; U.S. Pat. No. 4,335,723 to Patel describes the use of thermoplastic elastomer material for balloon cathers; U.S. Pat. No. 6,013,728 to Chen describes biocompatible polymers used in construction of vascular catheters and expansion balloons, U.S. Pat. No. 4,254,774 to Beritos teaches the manufacture of catheters with external diameters less than 1 mm and external balloons with walls less than 0.002 inches in thickness.

Preferably the retractor is a spherical balloon which has a diameter of 0.5 cm when inflated. The force that acts on the balloon comes from a 5 cm long shaft with an external diameter of 2 mm that passes through the center of the balloon. The retractor balloon is attached to the shaft in two places, where the shaft enters the balloon and at the tip of the shaft. These attachments are airtight and securely connect the balloon to the shaft.

At the exit of the shaft from the tongue there is a second balloon attached that serves as an anchor. The anchor balloon is 1 cm long and tapered with its narrow end embedded in tissue and the wider end outside tissue. The taper is a wedge which resists the anchor from being drawn into the tongue (FIG. 7). When the patient swallows the tongue curve rises and the anchor balloon is drawn into the tongue. After the swallow the anchor balloon gently repositions the device. The amount of resistance and counterforce provided by the anchor balloon is directly related to its degree of inflation. The greater the volume of air in the balloon the greater the resistance of the balloon to being drawn into the tongue.

The force imparted to the balloon indents the tissue at the tongue curve and prevents it from deforming and collapsing into the airway under negative pressure. This force is conveyed to the balloon by the shaft. This shaft passes through the center of the tongue to exit from the its undersurface at the point where the frenulum connects to the tongue blade.

The shaft is hollow with an internal diameter of 1 mm to allow it to be mounted over a trocar needle for insertion (FIG. 5). When the balloons are deflated they lie flush against the shaft such that the shaft has a smooth surface. In the deflated condition the device can be easily inserted or removed from the tongue. For example, in the morning the balloons can be deflated to slide the entire device out of the tongue. The presence of a tapered anchor balloon causes slight widening of the tongue tissue at its exit from the tongue. After a week this widening of the tissue is maintained even if the device is removed for a day and serves to easily guide the device into its tissue conduit. When the retractor tip is passed through the tongue and exits from the tongue base the balloons can be inflated to a proper size that is effective yet comfortable for the patient.

The balloons can be inflated separately or more preferably they are connected by a small tube that runs along the side of the shaft (FIG. 6). In this manner inflation of the anchor balloon, which is easily accessed by the patient, also inflates the retractor balloon. The anchor balloon has a small resealable rubber diaphragm through which a needle can be inserted to insert or remove air or liquid. U.S. Pat. No. 4,387,879 to Tauschinski describes a self-sealing connector for use with plastic cannulas and vessel catheters, U.S. Pat. No. 5,498,247 to Brimhall describes an elastomeric injection port that reseals after needle punctures for injection of fluid. A variety of other reusable interfaces for transferring air or fluid are known in the art and can be substituted.

A non-limiting example of the method of this invention is described. A 60 year male complains of awakening during the night with choking sensations, morning headaches, daytime sleepiness, difficulty in concentrating, irritability and acid reflux. Physical examination shows moderate obesity, an elongated soft palate and enlarged tongue base. Endoscopy shows diffuse mild swelling and redness throughout his pharyngeal mucosa. The area of the velopharynx is notably narrow and collapses when the patient attempts a forceful inspiration. The patient has a sleep study performed that shows he has obstructive sleep apnea with an apnea-hypopnea index of 30 with episodes of oxygen desaturation.

After discussing the therapeutic options with his physician he elects to try CPAP. He then undergoes a second overnight sleep study with CPAP testing and titration of pressure. He is found to have the best response a CPAP pressure of 14 cm of water. He obtains a CPAP machine and is instructed on its use. The patient finds that the device is uncomfortable, he complains of feeling claustrophobic and that it is difficult to maintain an airtight seal of the mask on his face throughout the night.

The patient requests that a tongue retractor be inserted. The procedure is performed in an ambulatory surgical center under mild sedation and with continuous monitoring of electrocardiogram and oxygen saturation.

A small amount of 1% lidocaine is sprayed onto the inferior surface of the patient's tongue to provide surface anesthesia. Using a 1 cc syringe with a 30 gauge needle the intended insertion tract in injected with suitable local anesthetic, preferably 1% lidocaine with 1:100,000 epinephrine. The needle is passed through the tongue from the undersurface to the tongue base and the anesthetic is injected.

After allowing 10 minutes for onset of the anesthetic action the physician gently grasps the tongue blade with a cotton 4×4 and lifts it to expose the undersurface of the tongue.

For initial insertion of the device it is mounted on a 5.25 cm trocar needle with a 1 mm external diameter. After the trocar is based through the hollow core of the device it covers the entire length of the trocar needle except thee tapered tip that projects 0.25 cm beyond the device.

The initial insertion point is at the junction of the frenulum with the tongue blade. The tip of the needle in inserted into the frenulum and oriented toward the tongue curve. The device is advanced slowly until it's tip is seen exiting the base of the tongue. The needle is pushed further until the retractor balloon is seen and then the needle is removed while the position of the device is maintained by holding the anchor. Once the needle is removed the balloons are inflated by injecting 2 cc of air though the resealable injection port. The patient is observed for 2 hours to ensure that no significant swelling occurs and then is sent home with mild analgesics and antibiotics for 3 days. Every morning the patient removes 1 cc of air from the device to decrease the size of the balloons so that the device is more comfortable. In the evening he reinjects 1 cc of air into the device.

After 1 week the patient returns to his physician for follow-up and reports that he has been sleeping well without awakening during the night and that feels well rested each morning without any headaches. His wife has told him that she has not noticed any snoring. The patient also notes that symptoms of acid reflux have decreased. The physician deflates the balloons and removes the device. He examines the openings of the tongue tract for any sign of infection or erosion. The physician then instructs the patient on how to remove and replace the device. From then on the patient completely deflates the balloons each morning and extracts the device by pulling on the anchor. In the evening he threads the retractor end into the tract opening underneath his tongue and then reinjects 2 cc of air.

This example is illustrative of a preferred embodiment and is not limiting. Non-limiting alternative embodiments include devices containing 1 to 10 balloons or a single balloon spanning the length of the shaft. The shaft itself may be composed of a solid or hollow cylindrical balloon. Those skilled in the art can perform the method of the device without undo experimentation. The device itself can be modified by the use of a variety of materials, and shape and nature of its components can be readily varied in multiple ways by those skilled in the art.

Example 2

Alternative Embodiment (FIG. 8)

In another embodiment of the invention used in the tongue the tongue retractor consists of a small flexible disc to which the retractor shaft connects in the center of one surface. This shaft would have a terminal end to which an anchor attached.

The disc would preferably be elliptical with a 1 cm long axis oriented along the centerline of the tongue, and a 5 mm short axis oriented perpendicular to the centerline. Preferably the undersurface of the retaining disc would have a slight taper in thickness from the lateral edges to the centerline.

The retaining disc would lay flush against the tongue surface and exert a small amount of force to prevent deformation of this area. More counterforce would cause an indentation or reverse deformation of the tongue curve (FIG. 8 D). This reverse deformation would maintain an open conduit so that even if the tongue were to collapse against the pharynx or soft palate, there would never be complete obstruction.

Preferably the disc would be composed of soft and pliable biocompatible material so that it can exert pressure onto tongue mucosa without causing tissue damage. The amount of pressure that an implant can exert without causing damage is largely related to the pressure at which blood flow is compromised. For the purpose of retaining the tongue curve the counter pressure is preferably 0.01 to 1000 grams per $cm^2$, more preferably 0.1 to 100 grams per $cm^2$, and most preferably 1 to 10 grams per $cm^2$.

The shaft would pass through the body of the tongue and exit through its undersurface. Preferably the shaft would be solid yet flexible, able to deform in shear and strain. This would allow the shaft to flex during when tongue movements cause internal changes in relative position along its length.

Preferably the shaft would be able to stretch. More preferably the shaft would be very compliant, able to easily stretch during forceful movements of the tongue base during speech and swallowing, yet retain sufficient strength to prevent deformation of the relaxed tongue curve during sleep. The force exerted by the tongue during swallowing has been measured to be approximately 100 grams per $cm^2$ (Proffit, W. R., Muscle pressures and tooth position: a review of current research. Aust. Orthod, J., 1973. 3: p. 104-108). Preferably the resistance to stretch would be adjustable by intrinsic qualities of the shaft. Non-limiting examples being the presence of a spring or by the use of elastomeric materials. In other embodiments the adjustment in tension and movement would be imparted by the anchor. A non-limiting example is a wedge shape similar to that described for the anchor balloon in the preferred embodiment.

Preferably the length of the shaft would be 1 mm to 20 cm, more preferable 1 to 10 cm and most preferably 5 cm. The diameter of the shaft could be from 0.1 mm to 5 cm. 1 mm in diameter and circular in cross section throughout most of its length.

Preferably the proximal end of the shaft has an anchor is detachable. The mechanism of attachment could be by screw, clip, ratchet, magnet, or other mechanism known in the art. In this manner the anchor could be either easily unattached from the anchor. When unattached the retractor head and shaft would preferably remain in position within the tongue. Preferably there would be a small flange on the anchor end of the shaft such as illustrated in FIG. 11 A.

If desired the device could be removed in its entirety during the day. After a period of time conduits that pass through body tissues become mature, that is they do not close immediately when the external object is removed temporarily. Therefore the device could be removed in the morning by pulling on the retaining disc leaving only the collapsed tract through tongue tissue. The following night the distal end would be again threaded through this tract into position and secured to the anchor.

Example 3

Alternative Embodiments Related to Soft Tissue Location

Although the tongue is the major cause of OSAS other soft tissue structures also contribute. Alternative embodiments of this invention can be used to prevent the deformation of lax soft tissue in these organs.

a) Placement of the Device in the Softpalate.

An elongated or thickened soft palate often contributes to OSAS or snoring. One embodiment of the invention is to reversible retract the soft palate tissue away from the area of obstruction to treat OSAS or snoring. Another object of the invention is to stiffen the soft palate to dampen its oscillation to prevent snoring. A preferred embodiment of the device in the soft palate would have a retractor on the external surface of the free end of the soft palate and a shaft passing forward within the soft palate to an anchor on the external surface of the soft palate near the hard palate (FIG. 10, SR). Numerous embodiments that achieve the object of the invention can be understood by those skilled in the art.

b) Placement of the Device in the Pharyngeal Walls

In certain cases excess soft tissue of the pharyngeal walls contributes to airway narrowing. The device can be inserted in pharyngeal walls to retract excess soft tissue away from the areas of obstruction (FIG. 10, SR).

c) Placement of the Device in Laryngeal Soft Tissue.

In certain cases the larynx contributes to OSAS. The epiglottis can be flail and rest against the posterior pharyngeal wall, or the soft tissue connected to the epiglottis, the aryepiglottic folds and vallecula, can be swollen. The internal side of these structures contains a dense sensory innervation and is hot a preferred location for retractor member. Most preferred is the mucosa of the vallecula, the area between the epiglottis and the tongue base. Retraction of this location raises the epiglottis and stiffens the soft tissue of the larynx.

Example 4

Alternative Embodiment that is Implanted within Soft Tissue

There are advantages to having the device pass completely through an upper airway organ. Without limitation these include easy access to the retractor and anchor components and the ability to easily remove the device. However, this is not essential. The device could also be completely implanted within tissue. Although not wishing to be bound by theory, the important action of the invention is to mechanically couple the soft tissue of a structure that relaxes during sleep to another structure. Preferably the second structure is an external muscle that remains active during sleep (genioglossus, geniohyoid, myelohyoid, digastric muscle) thereby providing active retraction. Other muscles within the neck (strenohyoid, sternothyroid, thryohyoid) and chest (diaphragm intercostals) could also be use however these would require long shafts. In the tongue one embodiment is a retractor implanted in the soft tissue of the tongue curve that is connected by a shaft to an anchor embedded in the genioglossus muscle (FIG. 9 C).

External retractors and anchors pull on mucosa and the underlying soft tissue. Their preferred mechanical interaction is to distribute force along a surface interface so as not cause pressure necrosis to tissue. In contrast, implanted embodiments can mechanically interface with tissue in additional ways.

FIG. 11 is an illustrative example of a an implantable device that has hook elements as both retractor and anchor components (FIG. 11A). The implanted device can be inserted using a hollow bore needle (FIG. 11 B) by placing the device such that the retractor end hooks extend laterally out from the opening of the needle near the tip (FIG. 11 C). Insertion can be done by piercing the mucosa at the site of insertion and passing the needle tip to the preferred depth. Then when the needle is withdrawn the hooks of the retractor grab tissue and pull the device out of the needle bore when the needle is withdrawn.

FIG. 11 D illustrates a preferred position and orientation within the tongue. The retractor hooks interface on soft tissue within the tongue so that they directly and indirectly can retract the tongue curve. The anchor hooks interface with the genioglossus muscle. During sleep the contraction of the genioglossus muscle actively retracts the tongue curve.

Example 5

Further Alternative Embodiments

The retractor components could vary in their number, position, material composition, mechanical properties, shape, dimensions, and the manner of attachment of the components to each other (permanent to removable).

In some embodiments the materials of the device could be flexible, non-limiting examples being silastic, teflon, or nylon. In other embodiments the materials could be rigid, non-limiting examples being stainless steel or titanium. In some embodiments different components are composed of different materials. Many biocompatible materials are known in the art that could be used. (Ratner et al, Biomaterials Science, Academic Press San Diego 1996). The materials used may be natural body substances, two common proteins used for implantation within the body are collagen and elastin and examples of the art using these materials are U.S. Pat. No. 5,989,244 to Gregory that describes the use of elastin as a material for implanted devices and U.S. Pat. No. 5,376,110 to Tu describing methods of preparing collagen for implants.

Preferably the retractor, anchor and shaft would be molded as a single continuous structure such that this junction would be less likely to have small niches where biological debris and bacteria could accumulate. In other embodiments components could be detachable. Many mechanisms for reversible mechanical detachment are known in the art, one non-limiting example is the presence of threads on the end of the shaft and in the center of the retractor head, such that that retractor head could be screwed onto the shaft like a nut onto a bolt.

In different embodiments the shape and size of the retractor would preferably reflect the anatomy of the region. In certain embodiments the retractor presses on the mucosal surface of the tongue, soft palate, pharyngeal walls, or supraglottic larynx. In these different embodiments the size and shape of the retractor could vary to conform to the shape of the surface that its rests against. Preferably the retractor would distribute force to the mucosa evenly to minimize tissue trauma. The largest diameter of the retractor head could range from 0.1 mm to 10 cm, preferably 1 mm to 1 cm and most preferably 5 mm.

The anchor serves to provide counterforce to the retractor during sleep. In a preferred embodiment the surface area of the bolster is the same or greater than the retractor thereby distributing the forces over a larger area. In some embodiments the anchor would serve to allow adjustment of tension between the anchor and the retractor.

In alternative embodiments the length of the shaft could vary from 0.1 mm to 20 cm, preferably 1 mm to 10 cm, and most preferably 1 to 5 cm. The diameter of the shaft could range from 0.01 mm to 100 mm, more preferably 0.1 mm to 10 mm, and most preferably 1 mm to 5 mm. The shaft could have a hollow core that extends from one end of the shaft to the other, in other embodiments only a segment of the shaft would be hollow, or the shaft would be solid with no hollow core. The diameter of the shaft could taper with the largest diameter at one end with decreasing diameter toward the other end, largest diameter in the center with narrowing toward each end or smallest diameter in the center with increasing diameters toward each end.

The position and orientation of the shaft could vary. The retractor head could be placed at other points along the midline of the tongue. The angle of the shaft could vary. In addition the shaft could be angled laterally to exit at any point lateral to the midline. The course of the shaft need not remain constant. It could start at one orientation and change to another.

In some embodiments the adjustment of tension between the retractor and the anchor would involve mechanically coupling the anchor to another object. This object could be another device implanted in another soft tissue area, teeth or dental appliances attached to the teeth, or objects external to the mouth. The component attaching the anchor to a second object could be a rubber band, a wire, string, chain, rod. Attachments could be by hooks, clips, magnets or other mechanical coupling methods known in the art.

One or both of the retaining components could be implanted such that the entire device would be implanted beneath the mucosa. In another embodiment, one end would be implanted and the other exit externally.

There could be multiple retractor heads and shafts in various combination. As an example a single retractor head at the tongue base could attach to two or more shafts. Areas through which the implant might be placed include the tongue, velopharyngeal, hypopharyngeal and nasopharyngeal walls, including the cheeks, hard and soft palate, and floor of the mouth. There may be one or more implants. The implant may retract the tissue by itself because of the area it is placed or may be attached to an another object by solid rods, wires, rubber bands. Non limiting examples are another device in the soft palate, cheek or lip, the teeth or intraoral dental devices, in addition the device can be attached to objects external to the mouth.

Example 6

The Device as a Conduit Between the Oral Cavity and Pharynx

In an alternative embodiment of the invention the shaft of the device is hollow and therefore functions as a conduit through the tongue. In those cases the device would more preferably be placed lower and oriented horizontally (FIG. 12). In this manner the shaft would pass parallel to the horizontal part of the genioglossus muscle or even lower through the geniohyoid or myelohyoid muscles. In this area of the tongue there is almost no tongue displacement in the superior or lateral direction, almost all movement is to shorten or lengthen in the anterior to posterior direction. As a result the conduit is not exposed to strong flexing forces, thereby allowing it to have a large diameter without interfering with tongue function.

In one alternative embodiment of the invention the shaft would be relatively larger and the retractor and anchor would be smaller, preferable reduced to a small flange around the edge of the openings to prevent the conduit from moving out of place (FIG. 12A). The anchor end in the mouth could have a removable cap and/or a connector to interface with other devices.

In one embodiment the conduit between the pharynx and mouth would allow passive equalization of air pressure in the pharyngeal space, attenuating the negative pressure that leads to collapse of the pharyngeal walls. Further embodiments would add mechanisms for sensing airflow or pressure that control a source of oxygen or air that could be delivered through the conduit. An attachment to an external pressure source could pump air to actively increase pharyngeal pressures. U.S. Pat. No. 5,954,050 to Christopher describes an invention where a conduit through the neck directly into the trachea is used to pass catheters capable of sensing airflow, pressure or carbon dioxide levels of the tracheal. These signals are all relevant indicators of sleep apnea and other respiratory diseases. In turn these signals could be used to control the delivery of oxygen or pressurized air.

A 60 year old male with severe obesity and OSAS yet declines a tongue retractor. Instead 1 cm removable conduit is be placed throughout the midline of the frenulum to the lower tongue base. The conduit is hollow and capped at the anterior end. At night the patient removes the cap and connects a 2 foot extension that connects to a small ventilator that delivers air continually through the conduit. The ventilator can be adjusted to deliver air at positive pressure. In an alternative embodiment the retractor end of the conduit has a sensor that measures pharyngeal pressure, carbon dioxide, and mechanical vibration, these signals are transferred to the ventilator by a wire running through the inside of the conduit and connection tubing, or sent by a small radio transmitter. The ventilator is programmed to recognize acute increases in negative pressure or carbon dioxide as indicative of airway obstruction while mechanical vibration indicates snoring. The signals triggers rapid delivery of air through the conduit to relieve the negative pressure.

Still further alternative embodiments of the invention are to introduce devices through the conduit that control the airway. Preferably these additional devices would be similar to the laryngeal mask or endotracheal tube by having a mechanism, preferably an inflatable balloon, that would occlude the airway around the tube. In this manner a controlled airway could be obtained for ventilation of the patient.

In further alternative embodiments the shaft of the conduit would be highly flexible so that after insertion it would be collapsed. However, an endotracheal tube or similar airway control device could be passed through the collapsed conduit easily. In this way patients who require temporary assisted ventilation could avoid having a tracheostomy tube placed (FIG. 15).

A non-limiting illustrative example is a 50 year old female with severe myasthenia gravis. The patient is able to breathe and swallow most of the time without assistance, however, almost every day she has periods where she feels weak and cannot breathe adequately. The patients has a conduit placed beneath her tongue in the centerline. The anchor is at the anterior floor of the mouth and the shaft passes between the genioglossus and geniohyoid muscles to the retractor end at the inferior aspect of the base of the tongue. The device is composed of soft reinforced silastic with a constant fully expanded diameter of 1 cm, however, after placement the surrounding tissue pressure causes it to collapse to a diameter of 2 mm. A cap that is also very flexible seals the anchor end. When not in use the device is comfortable and barely noticed by the patient and cannot be seen by other people. When the patient feels the need for assisted ventilation the cap can be opened to access the interior of the conduit. A ventilation tube of 8 mm external diameter is passed through the conduit into the hypopharynx. A balloon at the hypopharyngeal end of the ventilation tube can be inflated via a connector at its anchor end. The inflated balloon largely but does not completely block the hypopharynx above the opening of the tube, so there is some airleak when pressurized air is delivered through the tube. The patient connects the ventilator tube to a ventilator and adjusts the respiratory rate and tidal volume to comfortable levels. After two hours the patient feels stronger and turns the ventilator off, disconnects the tube, deflates the balloon and removes the ventilation tube.

Example 7

Suctioning Secretions

Many patients with neurological diseases have difficulty swallowing their salivary secretions and are at risk of aspiration and pneumonia. Moreover, some patients have excess pulmonary secretions that they cannot expel by themselves. It is well known in the art that suction catheters can be passed through the mouth or nose to suction secretions, however, these methods of suctioning secretions are extremely uncomfortable and labor intensive. If these methods are insufficient some patients undergo tracheotomy, intubation or other surgical procedures that allow more direct access for suctioning.

In an alternative embodiment the device can serve as a conduit to allow relatively easy suctioning of secretions. A flexible suctioning catheter could be inserted through the conduit to suction secretions from the hypopharynx or lungs. Alternatively an indwelling suction tube could be passed through the conduit such that it lies in the hypopharynx. The proximal end of said catheter is at the anchor end of the conduit and can be secured to the conduit by many mechanical means well known in the art. When necessary a source of negative air pressure could be attached to the conduit suction catheter. When not needed the negative pressure tube can be disconnected. In this manner suctioning could be easily performed at will with minimum discomfort to the patient. When the external tubing is disconnected the conduit would be unobtrusive.

In another embodiment of this invention a suction pump and energy supply is incorporated into the device. Secretions are suctioned from the floor of the mouth through the anchor side of the device. These secretions are passed to a catheter attached to the retractor end that passes into the esophagus or stomach. In this manner secretions are removed and appropriately delivered to the stomach before they cause a risk of aspiration to the patient.

Methods and devices representative of the prior art include U.S. Pat. No. 3,517,669 to Buono describes a valved device for suctioning secretions; U.S. Pat. No. 4,981,477 to Schon that describes a suction catheter for introduction into the trachea and the bronchial system; U.S. Pat. No. 5,694,922 describes methods and devices for accessing the resouratory system to ventilate the lungs of the patient with gas or gases, to aspirate secretions from the lungs, to oxygenate the lungs to eliminate or reduce residual $CO_2$ therefrom, to visually inspect selected parts of the respiratory system, to sample sputum and gases, to sense parameters such as flow rates, pressure, and temperature, to flush with washing solution, and/or to administer medication, gases, and/or lavage.

Example 8

Gastric or Pulmonary Tubes

Still another embodiment would be to use the device as an conduit for passing other tubes to the pharynx, esophagus, stomach or lungs.

Many patients with impaired swallowing require direct tube feeding into their stomachs. If the need for a tube is temporary the tube is passed through the nose and into the stomach (nasogastric tube). Generally the proximal attachment end of the tube is taped securely to the nose and also looped upward and taped directly to the face. At intervals liquid feedings are attached to the nasogastric tube. U.S. Pat. No. 4,704,111 to Moss describes one embodiment of a nasogastric feeding tube. If tube feedings are needed for a prolonged period a tube can be surgically implanted across the abdominal and into the stomach of small intestine (gastric tube). Both methods are uncomfortable, have significant complications, and impair the patient's mobility.

In one embodiment a thin wall tube could be passed through the shaft and extend into the esophagus or stomach (FIG. 13). In this embodiment direct gastric feeding could be done, eliminating the need for a nasogastric tube or percutaneous gastric tube. As the opening of the device is under the tongue it is not noticeable.

The implant may be temporary or permanent. It is one embodiment that part or all be removed during the day and replaced at night. The tissue conduit could be kept patent by a second item placed after the implant removal that was more comfortable.

In another embodiment the conduit is used to pass a temporary or permanent tube into the pharynx, larynx, trachea or lungs. Some patients with lung disease need supplemental oxygen. In another embodiment the tube could deliver medication locally to the structures of the upper airway or lung.

Example 9

Drug Delivery

The implant could also contain biologically active agents. Various inventions are known that store medication in reservoirs or pumps for controlled release and these could be incorporated into an embodiment of this invention. As an example of the art U.S. Pat. No. 5,976,109 to Heruth describe an implantable drug reservoir.

Another embodiment would have a drug that is useful for an entirely different purpose then sleep apnea. One example would be antibiotic for the treatment of peri-dontal disease. The antibiotic could be inserted into the conduit in biodegradable form or into a slow release pump, and would be released from the anchor end during the night to combat periodontal disease.

Another embodiment is medicine for gastrointestinal tract disease, a non-limiting example might be anti acid medication for acid reflux into the esophagus. This could be released directly from the retractor end into the pharynx. An additional embodiment would combine a sensor for pH and supply of the medication together, such that acidic pH could be sensed and treated efficiently.

Another embodiment is for the treatment of pulmonary disease. Currently, aerosolized medicines for lung diseases such as asthma or bronchitis are inhaled through the mouth. This is less efficient then direct delivery to the pharynx via the retractor side of the device, or to the trachea through catheters that pass from device to or through the larynx to the lungs. Medications preferably delivered by this method would include, without limitation, corticosteroids, bronchodilators, anti-inflammatory, mucolytic medications and antibiotics.

In another embodiment device could be releasing a medication that diffuses into the oral cavity or through the walls of the conduit into tongue tissue. U.S. Pat. No. 5,464,395 to Faxon describes a catheter for delivering therapeutic and/or diagnostic agents to the tissue surrounding a bodily passageway. An illustrative and non-limiting example might be a medication that reduces fat in the tongue base such as a mixture of phosphatidylcholine and sodium deoxycholate. These medicines have been injected subcutaneously to cause localized dissolution of fat (Rotunda, A M et al, (2004), Detergent effects of sodium deoxycholate are a major feature of an injectable phosphatidylcholine formulation used for localized fat dissolution. Dermatol Surg 2004; 30:1001-1008). Therefore the volume of the tongue base could be gradually decreased to improve OSAS. In an alternative embodiment the drug could be a chemotherapeutic agent for the treatment of cancer. As a further alternative embodiment the device would deliver radiation to a cancer of the soft tissue of the tongue, soft palate, pharynx or larynx. Representative examples of the prior art are U.S. Pat. No. 6,251,059 to Apple; U.S. Pat. No. 6,267,775 to Clerc describes a medical device for centering radioactive treatment sources in body vessels.

Example 8

Sensors and Neuroprosthetics

Sensors could be incorporated into the device to sense levels of gases or metabolites in the local blood flow around the device, which in turn reflect the systemic circulation. Alternatively sensors could detect the electrocardiogram, blood pressure, blood flow, position of the patient, vibration, temperature, tissue pressure or other physiological parameters. A transmitter could be incorporated within the device to transmit this signal to receivers outside the body. As a further embodiment the remote computer system would analyze the signals and send controlling signals back to the implanted device to control the release of drugs from the device, a neuroprosthetic device, or other medical device.

Examples of prior art are U.S. Pat. No. 6,636,769 to Govani describing an implanted sensor and telemetric system. U.S. Pat. No. 6,558,321 to Burd describing a system whereby the monitored signal is sent by telemetry to a remote computer which in turn sends signals back to control an implanted medical device; U.S. Pat. No. 5,109,850 to Bianco describes an implanted drug reservoir with a sensor that samples blood and controls the delivery of medication; U.S. Pat. No. 6,764,446 to Wolinsky describes an implant for surgical insertion in the mammalian body to monitor pressure or other physiological parameters and/or perform therapeutic functions, has a pressure sensor, controller, acoustic transducers, and an energy storage device A non-limiting example of this alternative a sensor in the device measures blood glucose levels, and in turn controls the release of appropriate amounts of insulin from a depot of this medication also incorporated into the device.

In another embodiment that treats OSAS the implant could have electrodes, battery power and stimulation electronics implanted to stimulate surrounding tissue. In one embodiment of the invention the implant contains sensors for negative pressure at the retractor end. These sensor detect airway obstruction. These signals in turn trigger electrical stimulation to the genioglossus muscle via surface electrodes on the exterior of the device in direct contact with the muscle. The stimulation causes contraction of the genioglossus muscle and anterior displacement of the tongue thereby relieving the obstruction.

In an alternative embodiment a patient has Parkinson's disease and has difficulty initiating a swallow when eating. An embodiment of the device is implanted that in the centerline of the tongue from the frenulum to the lower tongue base. The implant has a energy supply a receiver, and stimulation electronics. The retractor end of the device has electrodes on either side of a 1 cm flange in the valecullae. The patient has a small control unit that can send a signal to the device and cause electrical stimulation to excite sensory nerves in the valleculae thereby initiating a swallow.

Example 9

Surgical Access

Surgical procedures on the pharynx, larynx, lungs and esophagus have notably high morbidity. Although topologically these areas are outside the body the mouth and pharynx are a functional barrier to accessing these areas. As the neck contains so many different important structures surgical access almost invaribaly requires injuring normal structures. Moreover many surgical procedures, such as those for the treatment of cancer, are designed to accomplish their aims in the short time period that the interior of the body is accessible under anesthesia. Therefore surgical procedures are often more extensive they necessary. In contrast cancer that is located on the skin is often handled quite differently. The ready access to the area allows excision of minimum tissue, and repeated followup as necessary. In the upper airway almost all cancer begins on the surface. Therefore if access were easier some procedures on the pharynx and neighboring areas could be performed with less collatteral damage and shorter recovery times.

At present the technology for minimally invasive endoscopic surgery has advanced tremendously. Many procedures that once required wide incisions and large exposure are now performed through small percutaneous punctures using endoscopic and microsurgical equipment. The difference in morbidity and post operative recovery between the two methods are dramatic.

One alternative embodiment of this invention to provide conduits for surgical access to the pharynx and neighboring structures. In one embodiment the number, diameter and orientation of the conduits would be implanted specifically for the disease to be treated so as to provide maximum ease in performing endoscopic surgery. In a further embodiment these conduits could be accessed repeatedly over long periods of time to allow direct examination and continuing therapy.

As a non-limiting example a 65 year old male has a 2 cm ulcerated lesion of his pharyngeal wall. The lesion is biopsied and found to be squamous cell carcinoma. Medical and radiological examination suggest the lesion is localized to the pharyngeal wall and does not appear to have spread beyond the mucosa. After consultation with the patient on his treatment options it is decided to remove the lesion with endoscopic methods. Two collapsable conduits are implanted to access the lesion, the first passes through the centerline of the tongue from the frenulum to the midtongue base. The second passes through the skin of the undersurface of the jaw to enter at the base of the tongue 1 cm below the first conduit. The patients first procedure is performed under general anesthesia. Using a laser the lesion is vaporized via a rigid endoscope passed through the mouth. However, after the initial procedure the patient returns for followup examinations to the surgeons office every two weeks. Under minimal local anesthesia microsurgical endoscopes are passed through each conduit. Each is equipped with 1 mm fiber optic cable that delivers hi intensity illumination and captures video images. The surgeon examines the lesion closely and biopsies any suspicious tissue. When indicated the surgeon injects chemotherapeutic agents into and around the area biopsied. After six months the percutaneous conduit is removed and the patient is instructed to return monthly. After 1 year, no recurrence is evident and the second conduit is removed.

LEGEND TO DRAWINGS

| | |
|---|---|
| BA, Tongue base | a, anchor, |
| BD, Tongue body | ab, airway ballon |
| BL, Tongue blade | c, collar |
| Bo, Boundary between tongue and genioglossus | cc, collapsible conduit (cc) |
| C, Tongue curve | d, diaphragm, |
| F, Frenulum | h, handle |
| GG, Genioglossus muscle | i, injection port, |
| GT, Gastric tube | n, needle, |
| HP, Hypopharynyx | p, open end of tube |
| LR, Laryngeal soft tissue retractor | pa, pressurized air |
| NP, Nasopharynx | r, retractor balloon, |
| P, Hard palate | rc, resealable cap |
| PR, Pharyngeal wall retractor; | s, shaft, |
| PT, Pulmonary tube | sc, surgical conduit |
| SP, Soft palate | st, suction tube |
| SR, Soft palate retractor; | t, tube, |
| T, Tongue | v, vacuum source |
| VP, Velopharynx | |

What is claimed is:

1. A tissue retractor for treatment of at least one of snoring and sleep apnea in a patient that prevents deformation of a tongue of the patient, the tissue retractor comprising:
   a) a flexible shaft configured for transmucosal insertion into the patient's tongue;
   b) a retractor member connected at or near a first end of the flexible shaft; and
   c) an anchor member connected at or near a second end of the flexible shaft,
   wherein at least one of the retractor member or the anchor member is configured to be positioned on an external surface of the patient's tongue, and neither the retractor member nor the anchor member are configured to be tethered to bone,
   such that a tension from the flexible shaft is configured to exert an amount of pressure sufficient to prevent the external surface of the patient's tongue from falling toward a soft tissue located in an oral cavity or a pharynx of the patient when the patient's tongue is relaxed during sleep but permit flexing of the patient's tongue by not impairing normal movement of the patient's tongue during speech and swallowing,
   the tissue retractor further configured for at least one of removal, reinsertion, or subsequent retensioning by adjustment of the tissue retractor by the patient for effectiveness and comfort.

2. The tissue retractor of claim 1 wherein the flexible shaft is sized for insertion through the patient's tongue.

3. The tissue retractor of claim 1 wherein the exerted amount of pressure is a counterforce pressure that prevents deformation of the external surface of the patient's tongue, the exerted pressure is a counterforce pressure that creates an indentation in the external surface of the patient's tongue, or the retractor member, the flexible shaft, and the anchor member adjust to alter the counterforce pressure exerted on the patient's tongue.

4. The tissue retractor of claim 1 wherein the tissue retractor is formed from one or more biocompatible materials.

5. The tissue retractor of claim 1 wherein at least one of the retractor member, the flexible shaft, and the anchor member comprises an inflatable tube, or the flexible shaft comprises an internal passageway for adding a fluid.

6. The tissue retractor of claim 1 wherein the external surface of the patient's tongue is a centerline of a tongue curve.

7. The tissue retractor of claim 1 wherein at least one of the retractor member and the anchor member is disengageable from the flexible shaft.

8. The tissue retractor of claim 1 further comprising a connection configured to couple to at least one of the patient's pharynx, the patient's oral cavity, a tooth of the patient, a dental device, and a mount exterior to a mouth of the patient.

9. The tissue retractor of claim 1 wherein the tissue retractor is adjustable.

10. The tissue retractor of claim 1 wherein the anchor member is detachable from the flexible shaft.

11. A tissue retractor for treatment of sleep apnea in a patient that prevents a deformation of an external surface of a mucosa covering a soft tissue located in an oral cavity or a pharynx of the patient, the tissue retractor comprising:
   a) a flexible shaft configured for transmucosal insertion into the mucosa covering and the soft tissue;
   b) a retractor member connected at or near a first end of the flexible shaft; and
   c) an anchor member connected at or near a second end of the flexible shaft, wherein at least one of the retractor member or the anchor member is configured to be positioned on the external surface of the mucosa covering and the soft tissue, and neither the retractor member nor the anchor member are configured to be tethered to bone,
   such that a tension from the flexible shaft is configured to exert an amount of pressure sufficient to prevent the deformation of the external surface of the mucosa covering and the soft tissue when relaxed during sleep but permit flexing of the mucosa covering and the soft tissue by not impairing normal movement of the mucosa covering and the soft tissue during speech and swallowing,
   the tissue retractor further configured for at least one of removal, reinsertion, or subsequent retensioning by adjustment of the tissue retractor by the patient for effectiveness and comfort.

12. The tissue retractor of claim 11 wherein the flexible shaft comprises an internal passageway for adding a fluid.

13. The tissue retractor of claim 12 wherein the flexible shaft comprises a regulator for said fluid.

14. The tissue retractor of claim 11 wherein the exerted pressure is adapted to stiffen the mucosa covering and the soft tissue to prevent deformation of the external surface of the mucosa covering and the soft tissue, the exerted pressure is a counterforce pressure that prevents deformation of the external surface of the mucosa covering and the soft tissue, the exerted pressure is a counterforce pressure that creates an indentation in the external surface of the mucosa covering and the soft tissue, and at least one of the retractor member, the flexible shaft, and the anchor member are configured to be adjustable to alter the exerted pressure on the mucosa covering and the soft tissue.

15. The tissue retractor of claim 11 wherein at least one of the retractor member, the flexible shaft, and the anchor member comprises an inflatable tube.

16. The tissue retractor of claim 11 wherein at least one of the retractor member and the anchor member is disengageable from the flexible shaft.

17. The tissue retractor of claim 11 further comprising a connection configured to couple to at least one of the patient's pharynx, the patient's oral cavity, a tooth of the patient, a dental device, and a mount exterior to a mouth of the patient.

18. The tissue retractor of claim 11 wherein the tissue retractor is adjustable.

19. The tissue retractor of claim 11 wherein the anchor member is detachable from the flexible shaft.

20. A method for treatment of at least one of snoring and sleep apnea in a patient that prevents a deformation of a mucosa covering a soft tissue located in an oral cavity or a pharynx of the patient, the method comprising:
   a) inserting a flexible shaft, configured for transmucosal insertion, into the mucosa covering and the soft tissue of a tongue of the patient;
   b) connecting a retractor member at or near a first end of the flexible shaft; and
   c) connecting an anchor member at or near a second end of the flexible shaft, forming a connected retractor member, flexible shaft, and anchor member,
   wherein neither the retractor member nor the anchor member are configured to be tethered to bone, and at least one of the retractor member and the anchor member is positioned on an external surface of the patient's tongue, and at least one of the shaft, the retractor member and the anchor member interact such that a tension from the flexible shaft is configured to exert an amount of pressure sufficient to prevent the external surface of the patient's tongue from falling toward a soft tissue located in the patient's oral cavity or pharynx when the patient's tongue is relaxed during sleep but permit flexing of the patient's tongue by not impairing normal movement of the patient's tongue during speech and swallowing,
   the connected retractor member, flexible shaft, and anchor member further configured for at least one of removal, reinsertion, or subsequent retensioning by adjustment of the connected retractor member, flexible shaft, and anchor member by the patient for effectiveness and comfort.

21. The method of claim 20 wherein the amount of pressure creates an indentation in the external surface of the patient's tongue.

22. The method of claim 20 further comprising the step of:
   d) adjusting at least one of the retractor member, the shaft, and the anchor member to alter the amount of pressure.

23. The method of claim 20 wherein the first end of the flexible shaft is connected at or near a base of the patient's tongue and the second end of the flexible shaft is connected at or near a frenulum of the patient.

24. The method of claim 20 wherein the anchor member is in communication with a muscle that is active during sleep, or the anchor member is connected to at least one of a tooth of the patient's tooth, a dental device, and a mount exterior to the patient's oral cavity.

25. The method of claim 20 wherein at least a portion of at least one of the flexible shaft, the retractor member and the anchor member is positioned in an epiglottis of the patient, both the retractor member and the anchor member are positioned adjacent a superior surface of the patient's tongue, or the retractor member is on one side of a frenulum of the patient, the flexible shaft is beneath a tongue curve, and the anchor member is on the other side of the frenulum.

26. The method of claim 20 further comprising positioning the retractor member, the flexible shaft, and the anchor on a needle, inserting the needle to a desired depth within the patient's tongue, and removing the needle.

27. The method of claim 20 wherein step a) further comprises:
   a1) positioning the flexible shaft in a needle bore;
   a2) inserting the needle bore at or near a junction of a frenulum of the patient and the patient's tongue blade with a tip of the needle bore oriented toward the patient's tongue curve;
   a3) advancing the needle bore through the patient's tongue; and
   a4) removing the needle bore while maintaining the flexible shaft in the patient's tongue.

28. A method for treatment of a breathing disorder in a patient that prevents a deformation of an external surface of a mucosa covering a soft tissue located in an oral cavity or a pharynx of the patient, the method comprising:
   a) inserting a flexible shaft, configured for transmucosal insertion, into the mucosa covering and the soft tissue located in the patient's oral cavity or pharynx;
   b) connecting a retractor member at or near a first end of the flexible shaft; and
   c) connecting an anchor member at or near a second end of the flexible shaft, forming a connected retractor member, flexible shaft, and anchor member,
   wherein neither the retractor member nor the anchor member are configured to be tethered to bone, and at least one of the retractor member and the anchor member is positioned on an external surface of the soft tissue and at least one of the shaft, the retractor member and the anchor member interact such that a tension from the flexible shaft exerts an amount of pressure sufficient to prevent the deformation of the external surface of the mucosa covering and the soft tissue when relaxed during sleep but permit flexing of the mucosa covering and the soft tissue by not impairing normal movement of the mucosa covering and the soft tissue during speech and swallowing, the connected retractor member, flexible shaft, and anchor member further configured for at least one of removal, reinsertion, or subsequent retensioning by adjustment of the connected retractor member, flexible shaft, and anchor member by the patient for effectiveness and comfort.

29. The method of claim 28 wherein the amount of pressure is a counterforce pressure that creates an indentation in the external surface of the mucosa covering, the amount of pressure stiffens the mucosa covering and the soft tissue to prevent deformation of the external surface of the mucosa covering, or the pressure is amount of a counterforce pressure that prevents deformation of the external surface of the mucosa covering.

30. The method of claim 28 further comprising the step of:
   d) adjusting at least one of the retractor member, the shaft, and the anchor member to alter the amount of pressure.

31. The method of claim 28 wherein the anchor member is in communication with the external surface of the mucosa covering of a muscle in the patient's oral cavity that is active during sleep.

32. The method of claim 28 wherein the anchor member is connected to at least one of a tooth of the patient, a dental device, and a mount exterior to the patient's oral cavity.

33. The method of claim 28 wherein at least a portion of at least one of the flexible shaft, the retractor member and the anchor member is positioned in an epiglottis of the patient.

34. The method of claim 28 further comprising positioning the retractor member, the flexible shaft, and the anchor on a needle and inserting the needle to a desired depth within the soft tissue.

35. A tissue retractor for treatment of at least one of snoring and sleep apnea in a patient, the tissue retractor comprising:
   a) a flexible shaft configured for transmucosal insertion into a tongue of the patient;
   b) a retractor member connected at or near a first end of the flexible shaft, and
   c) an anchor member connected at or near a second end of the flexible shaft,
   wherein at least one of the retractor member or the anchor member is configured to be positioned on an external surface of the patient's tongue, and neither the retractor member nor the anchor member are configured to be tethered to bone,
   such that a tension from the flexible shaft is configured to exert an amount of pressure sufficient to prevent at least a portion of the patient's tongue from collapsing toward a soft tissue located in an oral cavity or a pharynx of the patient when the patient's tongue is relaxed during sleep but permit flexing of the patient's tongue by not impairing normal movement of the patient's tongue during speech and swallowing,
   the tissue retractor further configured for at least one of removal, reinsertion, or subsequent retensioning by adjustment of the tissue retractor by the patient for effectiveness and comfort.

36. The tissue retractor of claim 35 wherein the flexible shaft is removable from the patient's tongue.

37. The tissue retractor of claim 35 wherein the tissue retractor is adjustable.

38. The tissue retractor of claim 35 wherein the anchor member is detachable from the flexible shaft.

39. A tissue retractor for treatment of sleep apnea in a patient that prevents deformation of a soft tissue located in an oral cavity or a pharynx of the patient, the tissue retractor comprising:
   a) a flexible shaft configured for transmucosal insertion into the soft tissue;
   b) a retractor member connected at or near a first end of the flexible shaft; and
   c) an anchor member connected at or near a second end of the flexible shaft,
   wherein the retractor member and the anchor member are configured to maintain a position on an external surface of the soft tissue, and neither the retractor member nor the anchor member are configured to be tethered to bone,
   such that a tension from the flexible shaft is configured to exert an amount of pressure sufficient to prevent deformation of the external surface of the soft tissue when a tongue of the patient is relaxed during sleep but permit flexing of the patient's tongue by not impairing normal movement of the patient's tongue during speech and swallowing,
   the tissue retractor further configured for at least one of removal, reinsertion, or subsequent retensioning by adjustment of the tissue retractor by the patient for effectiveness and comfort.

40. The tissue retractor of claim 39 wherein the tissue retractor is adjustable.

41. The tissue retractor of claim 39 wherein the anchor member is detachable from the flexible shaft.

42. A method for treatment of a breathing disorder in a patient, the method comprising:

a) inserting a flexible shaft into a soft tissue located in an oral cavity or a pharynx of the patient;
b) connecting a retractor member at or near a first end of the flexible shaft; and
c) connecting an anchor member at or near a second end of the flexible shaft, forming a connected retractor member, flexible shaft, and anchor member, wherein each of the flexible shaft, the retractor member, and the anchor member contact solely soft tissue, neither the retractor member nor the anchor member are configured to be tethered to bone, and the shaft, the retractor member, and the anchor member interact such that a tension from the flexible shaft is configured to exert an amount of pressure sufficient to prevent deformation of an external surface of the soft tissue when a tongue of the patient is relaxed during sleep but permit flexing of the patient's tongue by not impairing normal movement of the patient's tongue during speech and swallowing, the connected retractor member, flexible shaft, and anchor member further configured for at least one of removal, reinsertion, or subsequent retensioning by adjustment of the connected retractor member, flexible shaft, and anchor member by the patient for effectiveness and comfort.

43. The method of claim 42 wherein the soft tissue is the patient's tongue, the retractor member contacts the patient's tongue, which retracts at least a portion of the patient's tongue curve, and the anchor member is implanted in a genioglossus muscle of the patient.

44. A device for treatment of a breathing disorder in a patient, the device having a first end, a second end, and a shaft disposed therebetween, the shaft is flexible and adapted for transmucosal insertion through a soft tissue located in an oral cavity or a pharynx of the patient, with at least one of the first end and the second end configured to maintain a position on an external surface of the soft tissue with each of the first end and the second end configured to contact solely the soft tissue, and such that a tension from the shaft is configured exert an amount of pressure sufficient to prevent deformation of at least a portion of the soft tissue to prevent obstruction in an airway of the patient when a tongue of the patient is relaxed during sleep but permit flexing of the patient's tongue by not impairing normal movement of the patient's tongue during speech and swallowing, the tissue retractor further configured for at least one of removal, reinsertion, or subsequent retensioning by adjustment of the device by the patient for effectiveness and comfort.

45. The device of claim 44 wherein both the first and the second end are configured to be positioned on an external surface of the soft tissue.

46. A method for treatment of at least one of snoring and sleep apnea in a patient that prevents a deformation of a mucosa covering a soft tissue located in an oral cavity or a pharynx of the patient, the method comprising:
a) inserting a flexible shaft into a tongue of the patient, a first end of the flexible shaft is connected at or near a base of the patient's tongue, and a second end of the flexible shaft is connected at or near a frenulum of the patient;
b) positioning a retractor member at or near the first end adjacent the base of the patient's tongue; and
c) positioning an anchor member at or near the second end adjacent the patient's frenulum, forming a connected retractor member, flexible shaft, and anchor member, wherein neither the retractor member nor the anchor member are configured to be tethered to bone, and the retractor member is positioned on an external surface of the patient's tongue, and the flexible shaft, the retractor member and the anchor member interact such that a tension from the flexible shaft is configured to exert an amount of pressure sufficient to prevent deformation of an external surface of the soft tissue when the patient's tongue is relaxed during sleep but permit flexing of the patient's tongue by not impairing normal movement of the patient's tongue during speech and swallowing, the connected retractor member, flexible shaft, and anchor member further configured for at least one of removal, reinsertion, or subsequent retensioning by adjustment of the connected retractor member, flexible shaft, and anchor member by the patient for effectiveness and comfort.

* * * * *

UNITED STATES PATENT AND TRADEMARK OFFICE
CERTIFICATE OF CORRECTION

| | |
|---|---|
| PATENT NO. | : 8,925,551 B2 |
| APPLICATION NO. | : 10/597590 |
| DATED | : January 6, 2015 |
| INVENTOR(S) | : Sanders |

Page 1 of 1

It is certified that error appears in the above-identified patent and that said Letters Patent is hereby corrected as shown below:

In the Claims

Column 26, lines 55-56, claim 24, delete "a tooth of the patient's tooth" and add --a tooth of the patient--.

Column 27, line 51, claim 29, delete "the pressure is amount of a counterforce pressure" and insert --the amount of pressure is a counterforce pressure--.

Signed and Sealed this
Twenty-eighth Day of July, 2015

Michelle K. Lee
*Director of the United States Patent and Trademark Office*